(12) United States Patent
Baker

(10) Patent No.: US 6,852,905 B2
(45) Date of Patent: Feb. 8, 2005

(54) FLUID HANDLING LAYERS MADE FROM FOAM AND ABSORBENT ARTICLES CONTAINING SAME

(75) Inventor: Andrew Baker, Lawrenceville, GA (US)

(73) Assignee: Paragon Trade Brands, Inc., Norcross, GA (US)

( * ) Notice: Subject to any disclaimer, the term of this patent is extended or adjusted under 35 U.S.C. 154(b) by 72 days.

(21) Appl. No.: 09/987,762

(22) Filed: Nov. 15, 2001

(65) Prior Publication Data

US 2003/0093050 A1 May 15, 2003

(51) Int. Cl.⁷ ............................................. A61F 13/15
(52) U.S. Cl. ..................................................... 604/369
(58) Field of Search .................................. 604/369, 378

(56) References Cited

U.S. PATENT DOCUMENTS

| | | |
|---|---|---|
| 2,537,685 A | 1/1951 | Matheson |
| 2,552,350 A | 5/1951 | Smith |
| 3,124,605 A | 3/1964 | Wagner |
| 3,152,162 A | 10/1964 | Fischer et al. |
| 3,183,112 A | 5/1965 | Gemassmer |
| 3,358,010 A | 12/1967 | Britain |
| 3,563,243 A | 2/1971 | Lindquist |
| 3,644,490 A | 2/1972 | Schmelzer et al. |
| 3,699,103 A | 10/1972 | Kiss |
| 3,769,318 A | 10/1973 | Windemuth et al. |
| 3,770,731 A | 11/1973 | Jaeger |
| 3,862,973 A | 1/1975 | Dietrich et al. |
| 3,903,127 A | 9/1975 | Wagner et al. |
| 3,906,126 A | 9/1975 | Kaiser et al. |
| 4,050,462 A | 9/1977 | Woon et al. |
| 4,051,165 A | 9/1977 | Wagner et al. |
| 4,147,714 A | 4/1979 | Hetzel et al. |
| 4,160,080 A | 7/1979 | Köenig et al. |
| 4,177,342 A | 12/1979 | Bock et al. |
| 4,220,749 A | 9/1980 | Reichmann et al. |
| 4,288,586 A | 9/1981 | Bock et al. |
| 4,300,562 A | 11/1981 | Pieniak |
| 4,323,069 A | 4/1982 | Ahr et al. |
| 4,324,246 A * | 4/1982 | Mullane et al. ............. 128/287 |
| 4,324,879 A | 4/1982 | Bock et al. |
| 4,554,297 A | 11/1985 | Dabi |
| 4,646,362 A | 3/1987 | Heran et al. |
| 4,673,402 A | 6/1987 | Weisman et al. |
| 4,740,520 A | 4/1988 | Hallenbach et al. |
| 4,935,022 A | 6/1990 | Lash et al. |
| 4,950,264 A | 8/1990 | Osborn, III |
| 5,092,861 A | 3/1992 | Nomura et al. |
| 5,098,423 A | 3/1992 | Pieniak et al. |
| 5,124,427 A | 6/1992 | Potter et al. |
| 5,147,345 A | 9/1992 | Young et al. |
| 5,147,897 A | 9/1992 | Morimoto et al. |
| 5,164,421 A * | 11/1992 | Kiamil et al. ................ 521/159 |
| 5,208,334 A | 5/1993 | Potter et al. |
| 5,235,018 A | 8/1993 | Potter et al. |
| 5,260,345 A | 11/1993 | DesMarais et al. |
| 5,268,224 A | 12/1993 | DesMarais et al. |

(List continued on next page.)

FOREIGN PATENT DOCUMENTS

| | | |
|---|---|---|
| EP | 0198683 | 10/1986 |
| WO | WO 01/55242 | 8/2001 |

*Primary Examiner*—Larry I. Schwartz
*Assistant Examiner*—C. Lynne Anderson
(74) *Attorney, Agent, or Firm*—Hunton & Williams

(57) ABSTRACT

The Invention relates to absorbent articles, such as diapers, incontinence products, training pants, sanitary napkins, and the like, providing superior strikethrough and rewet characteristics, and methods of preparing the absorbent articles. The absorbent articles comprise at least a topsheet, backsheet, absorbent core, and fluid handling layer, and the article has a third insult Strikethrough of less than about 45 seconds, and a third insult Rewet of less than about 35 grams.

71 Claims, 8 Drawing Sheets

U.S. PATENT DOCUMENTS

| | | | |
|---|---|---|---|
| 5,281,207 A | 1/1994 | Chmielewski et al. | |
| 5,310,554 A | 5/1994 | Haigh | |
| 5,318,554 A | 6/1994 | Young et al. | |
| 5,331,015 A | 7/1994 | DesMarais et al. | |
| 5,352,217 A | 10/1994 | Curro | |
| 5,352,711 A | 10/1994 | DesMarais | |
| 5,502,147 A | 3/1996 | Nodelman et al. | |
| 5,550,167 A | 8/1996 | DesMarais | |
| 5,603,707 A | 2/1997 | Trombetta et al. | |
| 5,632,737 A | 5/1997 | Stone et al. | |
| 5,692,939 A | 12/1997 | DesMarais | |
| 5,719,201 A * | 2/1998 | Wilson | 521/137 |
| 5,786,395 A | 7/1998 | Stone et al. | |
| 5,786,396 A | 7/1998 | Takita et al. | |
| 5,803,920 A | 9/1998 | Gilman | |
| 5,817,703 A * | 10/1998 | Blair et al. | 521/53 |
| 5,830,203 A | 11/1998 | Suzuki et al. | |
| 5,840,780 A * | 11/1998 | Wilson | 521/137 |
| 5,851,648 A | 12/1998 | Stone et al. | |
| 5,863,288 A | 1/1999 | Baker | |
| 5,895,379 A * | 4/1999 | Litchholt et al. | 604/378 |
| 6,068,620 A | 5/2000 | Chmielewski | |
| 6,099,950 A | 8/2000 | Wang et al. | |
| 6,121,509 A | 9/2000 | Ashraf et al. | |
| 6,140,550 A * | 10/2000 | Beihoffer et al. | 604/366 |
| 6,171,291 B1 | 1/2001 | Osborn, III et al. | |
| 6,224,961 B1 | 5/2001 | Hsueh et al. | |
| 6,417,425 B1 * | 7/2002 | Whitmore et al. | 604/367 |
| 6,545,195 B2 * | 4/2003 | Chmielewski | 604/369 |

* cited by examiner

Top Sheet cut and transfer layer removed

FLUID HANDLING LAYERS MADE FROM FOAM AND ABSORBENT ARTICLES CONTAINING SAME

BACKGROUND OF THE INVENTION

1. Field of the Invention

The present invention relates generally to an absorbent composition for absorbent articles such as diapers, incontinence products, training pants, sanitary napkins, and the like. In particular, the present invention relates to an absorbent article that has good strikethrough and rewet properties.

2. Description of Related Art

Disposable absorbent articles typically include a moisture-impervious backing sheet, an absorbent pad, and a liner sheet that contacts the body of a person wearing the article. In addition, elasticized regions are provided around the edges of the article to secure the article about the waist and legs of a wearer. Absorbent articles such as diapers typically further comprise opposed front and rear waist portions defining a waist opening, a crotch portion disposed there between, and a pair of elastically contractible leg openings along the side edges of the crotch portion. Disposable diapers having elasticized margins for placement about the legs of a wearer are disclosed in U.S. Pat. No. 4,050,462 and U.S. Pat. No. 5,092,861, the disclosures of which are incorporated by reference herein in their entirety. An absorbent article having elasticized side margins and waist band margins are described in U.S. Pat. No. 4,300,562, the disclosure of which is incorporated by reference herein in their entirety.

Despite previous advancements in the field of absorbent articles, there still is a current need to provide absorbent articles that are better able to contain urinary and fecal excretions. For instance, problems with prior diaper designs include inferior absorbency and leakage of urinary or fecal material from the article. Prolonged contact of liquid or semi-solid excreta with the skin of the wearer is also a continuing problem. For example, the moisture vapor and heat generated by the bodily exudate trapped within a diaper may lead to conditions adjacent to the wearer's skin that promotes skin irritation, infection, and the like.

Developing highly absorbent articles for use as disposable diapers, adult incontinence pads and briefs, and catamenial products such as sanitary napkins typically entails developing relatively absorbent cores or structures that can acquire, distribute and store large quantities of discharged body fluids, in particular urine. For example, absorbent structures include particulate absorbent polymers often referred to as "hydrogels," "superabsorbents" or "hydrocolloid" materials. See, for example, U.S. Pat. No. 3,699,103, and U.S. Pat. No. 3,770,731 that disclose the use of such particulate absorbent polymers in absorbent articles. Indeed, the development of high performance diapers has been due in part to thinner absorbent cores that take advantage of the ability of these particulate absorbent polymers to absorb large quantities of discharged aqueous body fluids, typically when used in combination with a fibrous matrix. See, for example, U.S. Pat. No. 4,673,402 and U.S. Pat. No. 4,935,022, that disclose dual-layer core structures comprising a fibrous matrix and particulate absorbent polymers useful in fashioning high performance diapers.

Other absorbent materials capable of providing good absorbency and good capillary fluid transport are open-celled polymeric foams. Certain types of polymeric foams have been used in absorbent articles for the purpose of imbibing, and/or wicking aqueous body fluids. See, for example, U.S. Pat. No. 3,563,243 (absorbent pad for diapers and the like where the primary absorbent is a hydrophilic polyurethane foam sheet); U.S. Pat. No. 4,554,297 (body fluid absorbing cellular polymers that can be used in diapers or catamenial products); U.S. Pat. No. 4,740,520 (absorbent composite structure such as diapers, feminine care products and the like that contain sponge absorbents made from certain types of super-wicking, crosslinked polyurethane foams).

There are a number of documents describing absorbent foams, for example, those that have been made from High internal Phase Emulsions (hereafter referred to as "HIPE"), or those made from hydrophilic, flexible, open-celled foam such as a melamine-formaldehyde foam (e.g., BASO-TECT™ made by BASF). See, for example, U.S. Pat. Nos. 5,147,345, 5,260,345, 5,268,224, 5,318,554, 5,331,015, 5,352,711, 5,550,167, 5,632,737, 5,692,939, 5,786,395, and 5,851,648. Some of these foams provide desirable fluid handling properties, including: (a) relatively good wicking and fluid distribution characteristics to transport the imbibed urine or other body fluid away from the initial impingement zone and into the unused balance of the foam structure to allow for subsequent gushes of fluid to be accommodated; and (b) a relatively high storage capacity with a relatively high fluid capacity under load, i.e. under compressive forces. These HIPE absorbent foams are also sufficiently flexible and soft so as to provide a high degree of comfort to the wearer of the absorbent article; some can be made relatively thin until subsequently wetted by the absorbed body fluid.

U.S. Pat. Nos. 5,147,345, and 5,310,554 to Young et al. discloses absorbent articles, such as diapers, for the management of incontinence. Such articles utilize in their absorbent cores a fluid acquisition/distribution component and a fluid storage/redistribution component maintained in fluid communication with the acquisition/distribution component. The fluid acquisition/distribution component can be any porous hydrophilic, e.g., fibrous or foam-based, material which will provide an initial Fluid Acquisition Rate of at least 2 mL of synthetic urine per second and will also preferably provide a 30-minute Vertical Wicking Height of at least 2 cm. The fluid storage/redistribution component comprises a hydrophilic, flexible, open-celled polymeric foam having a free absorbent capacity of at least about 12 mL of synthetic urine per gram of dry foam and an absorbent capacity under a 5.1 kPa confining pressure which is at least 5% of this free capacity. Preferred fluid acquisition/distribution component materials comprise chemically stiffened, twisted, curled cellulosic fibers. Preferred fluid storage/redistribution component materials comprise absorbent foams prepared by polymerizing a high internal phase emulsion (HIPE).

U.S. Pat. Nos. 5,268,224, and 5,331,015 to Des Marais et al. discloses absorbent foam materials suitable for use as or in the absorbent cores of absorbent articles, such as diapers which absorb and retain aqueous body fluids. Such foam materials comprise hydrophilic, flexible open-celled structures which are preferably prepared by polymerizing high internal phase (HIPE) water-in-oil emulsions. Such foam materials have a pore volume of from about 12 to 100 mL/g, and a capillary suction specific surface area of from about 0.5 to 5.0 m$^2$/g. These materials also exhibit a resistance to compression deflection such that a confining pressure of 5.1 kPa produces after 15 minutes a strain of from about 5% to 95% compression when the material is saturated at 37° Celsius to its free absorbent capacity with synthetic urine.

U.S. Pat. Nos. 5,851,648, 5,786,396, 5,632,737, 5,692, 939, and 5,550,167 disclose absorbent foams materials that are capable of acquiring and distributing aqueous fluids, especially discharged body fluids such as urine. These absorbent foams combine relatively high capillary absorption pressures and capacity-per-weight properties that allow them to acquire fluid, with or without the aid of gravity. These absorbent foams are alleged to give up this fluid to higher absorption pressure storage materials, including foam-based absorbent fluid storage components, without collapsing. These absorbent foams are made by polymerizing high internal phase emulsions (HIPEs).

U.S. Pat. No. 5,352,711 to Des Marais discloses that normally hydrophobic foams and polymerized water-in-oil emulsion foams are rendered hydrophilic by means of treatment with simple surfactants and hydrophilizing agent salts. Thus, a surfactant-containing foam is treated with a solution of, for example, calcium chloride, and is dried to leave a substantially uniformly distributed residue of hydrated or hydratable calcium chloride on the surfactant-containing internal foam surfaces. In-use, the combination of surfactant and calcium chloride hydrate provides a hydrophilic surface to the foam. Other hydratable calcium or magnesium salts such as magnesium chloride can be used. The resulting hydrophilized foams are said to be suitable for use in absorbent devices, including diapers, sanitary napkins, bandages, and the like.

Polyurethane foams are known to be useful as absorbent materials. For example, U.S. Pat. No. 5,164,421 discloses a hydrophilic foam that is applicable for the manufacture of absorptive devices. The hydrophilic polyurethane foams can be made from aromatic polyisocyanates.

A desirable feature of absorbent articles is that they should exhibit good strikethrough and low rewet characteristics, permitting bodily discharges to rapidly penetrate there through, but not flow back through to the skin of the wearer. Rewet has many causes. Typically, rewet occurs when the absorbent core of the article becomes saturated and unable to hold more fluid. Rewet also occurs when the absorbent core is below its saturation point. For example, rewet may occur when the absorbent core can not absorb a given volume of fluid quickly enough. Rewet also may occur when an absorbent article is placed under pressure, causing fluid to be mechanically forced out of the absorbent core. Typically, when an absorbent article is at a high saturation level or at the saturation point, rewet becomes an increased problem, as the compressive force required to force fluid out of the absorbent core decreases.

One suggested solution to reduce the rewet characteristics of absorbent articles is to provide an acquisition or transport layer between the absorbent core and the liquid permeable body contacting layer (e.g., topsheet). The acquisition layer distributes fluids across the surface of the absorbent core to improve the absorbent core's ability to rapidly absorb fluids. Once the fluids are absorbed by the core, the acquisition layer acts as a relatively dry boundary between the topsheet and the absorbent core to prevent rewet. This benefit is minimal, however, because conventional acquisition layers do not prevent fluid from reemerging from the core when the core is placed under pressure, especially when the core is at or near the saturation point. Rewet therefore typically occurs under these circumstances.

Another suggested solution is to provide an apertured film layer to prevent backflow of fluid out of the absorbent core. Apertured films having three-dimensional funnels have been found to provide preferential fluid flow away from the surface of the film and through the funnels. Such films may provide beneficial rewet capabilities when properly employed in the construction of an absorbent article. U.S. Pat. No. 6,171,291, issued to Palumbo et al., discloses the use of an apertured film body-contacting topsheet to prevent rewet. It has been recognized, however, that the use of an apertured film as a topsheet may necessitate careful selection of or additional modifications to the apertured film to provide the apertured film with a suitable feel and texture for use as a body-contacting surface. These and other considerations significantly increase the cost of the article, and/or reduce design flexibility.

An apertured layer may also be used as a rewet barrier located between the topsheet and the absorbent core. U.S. Pat. No. 5,603,707, issued to Trombetta, et al., discloses an absorbent article having a macroscopically expanded apertured web acting as a rewet barrier disposed between the absorbent core and an additional fibrous acquisition layer located adjacent the topsheet. U.S. Pat. No. 4,323,069, issued to Ahr et al., also discloses an intermediate layer comprising capillary openings, located between a fibrous acquisition layer and an absorbent core. U.S. Pat. No. 5,352,217, issued to Curro, discloses the use of multiple layers of apertured film topsheets to reduce rewet.

It is desirable to provide cost-efficient absorbent articles that display superior absorbency, as well as novel compositions and composites for use in the absorbent articles. Further, it is desirable to provide a cost-efficient process for producing absorbent articles having superior absorbency. It is worth noting here, that even despite the aforementioned disadvantages, nothing stated herein detracts from the usefulness or possibility that any of these materials may be used in conjunction with the present invention.

The documents described above are incorporated herein by reference in their entirety.

SUMMARY OF THE INVENTION

The present invention provides absorbent articles, and compositions and composites for use in same, that display superior absorbency, and that have good Strikethrough and Rewet characteristics. Further, the present invention provides a process for producing absorbent articles having, inter alia, the aforementioned desirable properties.

It is a feature of an embodiment of the invention to provide an absorbent article having a fluid transport layer that has both good Strikethrough and Rewet characteristics. It also is a feature of an embodiment of the invention to provide a method of making an absorbent article having a fluid transport layer that has both good Strikethrough and Rewet characteristics.

In accordance with these and other features of various embodiments of the present invention, there is provided an absorbent article comprising at least a topsheet, a backsheet, an absorbent core disposed between the topsheet and backsheet, and a fluid transport layer disposed between the topsheet and the absorbent core. The absorbent article has a third insult Strikethrough of less than about 45 seconds, and a third insult Rewet of less than about 35 grams.

In accordance with an additional feature of an embodiment of the invention, there is provided a method of making an absorbent article comprising providing a topsheet material and a backsheet material, and disposing between the topsheet and backsheet materials an absorbent core. The method also includes disposing between the topsheet and the absorbent core a fluid transport layer, whereby the absorbent article has a third insult Strikethrough of less than about 45 seconds, and a third insult Rewet of less than about 35 grams.

DETAILED DESCRIPTION OF PREFERRED EMBODIMENTS

Figure 1:
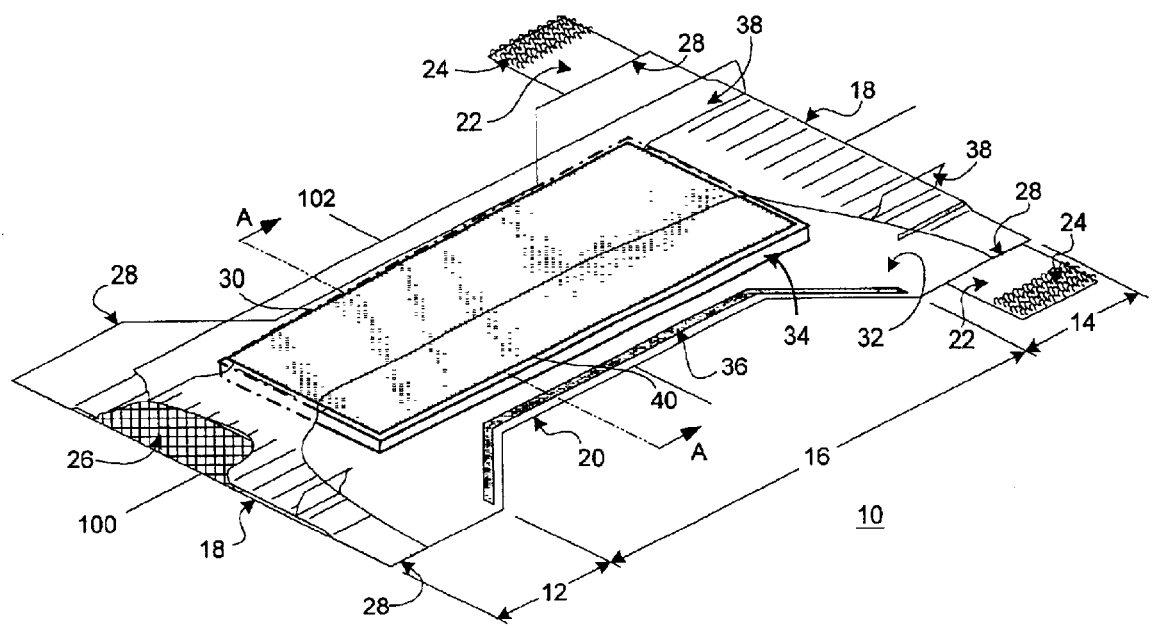
FIG. 1 is a schematic view of an absorbent article for use in the present invention.

As used herein, the term "absorbent article" refers to articles that absorb and contain exudates, and more specifically refers to articles that are placed against or in proximity to the body of a wearer of the absorbent article to absorb and contain various exudates discharged from the body. A non-exhaustive list of examples of absorbent articles includes diapers, diaper covers, disposable diapers, training pants, feminine hygiene products and adult incontinence products, without limitation. The term "disposable article" refers to absorbent articles that are intended to be discarded or partially discarded after a single use, i.e., they are not intended to be laundered or otherwise restored or reused. The term "unitary disposable absorbent article" refers to a disposable absorbent article that is essentially a single structure (i.e., it does not require separate manipulative parts such as a diaper cover and insert). As used herein, the term "diaper" refers to an absorbent article generally worn by infants and incontinent persons about the lower torso.

The claims are intended to cover all of the forgoing classes of absorbent articles, without limitation, whether disposable, unitary or otherwise. These classifications are used interchangeably throughout the specification, but are not intended to limit the claimed invention. The invention will be understood to encompass, without limitation, all classes of absorbent articles, including those described above. Preferably, the absorbent core is thin in order to improve the comfort and appearance of a garment. Employing thin, comfortable garments is disclosed, for example without limitation in U.S. Pat. No. 5,098,423 to Pineiak et al., which is herein incorporated by reference in its entirety.

The term "Strikethrough" is used herein to denote the amount of time it takes for liquid to pass through the material being tested. Strikethrough is a measure of the fluid acquisition properties of the material. Strikethrough is measured in accordance with the test procedures defined below. Unless indicated otherwise, Strikethrough values are reported herein in seconds.

The term "Rewet" is used herein to mean retransmission of liquid from the absorbent core to the body or wearer side of the topsheet when the disposable absorbent article is in use. Rewet therefore is a measure of the absorbent article's fluid retention capabilities under load. Low Rewet means low retransmission of liquid from the fluid transport layer and/or absorbent core to the body or wearer side of the topsheet. The Rewet property of an absorbent article is determined by the procedure outlined in the test procedures section below. Unless indicated otherwise, Rewet values are reported herein in grams.

The present invention provides an absorbent article, as well as a method of preparing the same and a method of using the absorbent article. The absorbent article has superior properties of absorbency, leakage protection and/or skin wellness, as well as being aesthetically pleasing. These properties are a feature of the fluid transfer layer's ability to rapidly acquire fluid, and then to retain the fluid and redistribute it to the absorbent code while under load.

Those skilled in the art recognize that a material that has a good Strikethrough characteristic typically has poor fluid retention (e.g., Rewet) characteristics. This is because good Strikethrough is a measure of how fast the material can acquire fluid. Materials that can quickly acquire fluid typically are quite porous, have good wicking properties, and/or have well defined fluid flow channels. Consequently, these materials by design typically lose their fluid as quickly as they acquire it, which translates to poor Rewet, or poor fluid retention.

As mentioned earlier, prior disclosures describing the use of foam materials typically required two different materials: (i) one having good fluid acquisition properties (e.g., good Strikethrough); and (ii) the other having good fluid retention properties (e.g., good Rewet). It is therefore surprising and unexpected that absorbent articles having the fluid transfer layer of the invention that preferably, but not necessarily, are comprised of at least a foam material, more preferably at least an aliphatic isocyanate-derived polyurethane foam material, has both good Strikethrough and Rewet properties.

The invention preferably comprises an absorbent article having at least a topsheet, a backsheet, an absorbent core disposed between the topsheet and backsheet, and a fluid transport layer disposed between the topsheet and the absorbent core. The fluid transport layer preferably is comprised of at least one foam material, and more preferably at least an aliphatic isocyanate-based polyurethane foam material. In the present invention, the absorbent article preferably has a third insult Strikethrough of less than about 45 seconds, and a third insult Rewet of less than about 35 grams. More preferably, the absorbent article has a third insult Strikethrough of less than about 405 seconds, and a third insult Rewet of less than about 30 grams, and most preferably, third insult Strikethrough of less than about 35 seconds, and a third insult Rewet of less than about 25 grams. Although described together, the preferred absorbent articles need not have the same combination of preferred Strikethrough and Rewet, thus enabling an absorbent article having, say, a third insult Strikethrough of less than about 30 seconds, and a third insult Rewet of less than about 35 grams.

It is preferred in the present invention to characterize the absorbent articles by their third insult Strikethrough and Rewet values. This is believed to be because many materials will have comparable first insult Strikethrough and Rewet values, but materials that prevent leakage will differentiate from the other materials at the second and third insult values. In addition, first insult Strikethrough and Rewet data does not provide much information about an absorbent article in a stressed condition (e.g., at the upper end of the capability of the article). Thus, first insult Strikethrough and Rewet values are not necessarily good predictors of materials that will have good third insult Strikethrough and Rewet. In addition, it is not practical to change an absorbent article after the first insult, and in the evening, three or more insults typically occur prior to changing the absorbent article. Consequently, absorbent articles having good third insult Strikethrough and Rewet will be more suitable for extended use absorbent articles. Moreover, it is believed that absorbent garments that have low third insult Rewet values keep the skin dryer immediately after use, and since dry skin helps keep the skin healthy, consumers recognize low rewet as a benefit. Finally, it is believed that absorbent garments having low third insult Strikethrough can improve the leakage performance of the absorbent article.

The absorbent article now will be described in more detail with reference to the attached Figures. For clarity, features that appear in more than one Figure have the same reference number in each Figure.

FIG. 1 is a partially cut away depiction of an exemplary embodiment of a garment 10 of the present invention. The embodiment shown in FIG. 1 is an infant's diaper, however, this depiction is not intended to limit the invention. The garment 10 of FIG. 1 is depicted in a flattened position, with the various elastic components depicted in their extended position for clarity. In the flattened position, the garment 10 generally has an hourglass shaped structure, but it may also have a rectangular or trapezoidal shape.

As used herein, the longitudinal axis 100 of the garment is the dimension of the garment corresponding to the front-to-rear dimension of the user, and the lateral axis 102 of the garment is the dimension corresponding to the side-to-side dimension of the user.

In use, an embodiment of the absorbent article of the invention is a pant-like garment 10 having a waist-encircling region and a crotch region. The waist-encircling region may comprise a front region 12, corresponding to the front of a wearer's body, and a rear region 14, corresponding to the back of a wearer's body, that are joined together at or near their lateral edges 28, causing the longitudinally distal edges 18 of the garment 10 to form the perimeter of a waist opening. The crotch region 16 extends between the front and rear regions 12, 14, and the crotch edges 20 form the perimeter of a pair of leg openings.

The front and rear regions 12, 14 may be joined to one another by permanent seams (not shown) or by releasable fasteners 22. The releasable fasteners 22 may comprise an adhesive tape, a mechanically interlocking fastener, such as a hook and loop fastener 24 or a button or snap, or any other suitable releasable fastening device (e.g., string, twist tie, etc.). The garment may also comprise a target surface 26 associated with a surface of the garment 10, that is selected to interact with the releasable fasteners 22 to provide them with the grip necessary to hold the garment 10 together. While the embodiment depicted in FIG. 1 shows the releasable fasteners 22 being located in the rear region 14, and the target surface 26 being in the front region 12, skilled artisans will recognize that these locations may be reversed. While the embodiment shown in FIG. 1 shows a hook and loop fastener 22, 24, those skilled in the art will appreciate that any fastening mechanism 22 can be used in the present invention. The selection and manufacture of permanent side seams, releasable fasteners 22, and target surfaces 26 is known in the art, and a skilled artisan can produce such structures and devices without undue experimentation.

The garment 10 preferably comprises a topsheet 30, and a backsheet 32, which may be substantially coterminous with the topsheet 30. When the garment 10 is being worn, the topsheet 30 faces the wearer's body, and the backsheet 32 faces away from the wearer. A foam fluid handling layer 40 preferably is located between the topsheet 30 and the backsheet 32, whereby the foam material preferably is an aliphatic isocyanate-derived polyurethane foam. The fluid handling layer 40 may extend from the front region 12, through the crotch region 16, and into the rear region 14, and can be attached to the garment 10 in at least one of the front region 12 and the rear region 14. A particularly preferred configuration of the invention contemplates one in which the lateral width and longitudinal length of the fluid handling layer 40 are slightly smaller than the respective width and length of the underlying absorbent core 34. It may be beneficial in the invention that at least one longitudinal end of the fluid handling layer 40 be extended prior to being attached to the garment 10, such that when the fluid handling layer 40 contracts it causes the garment to shirr or gather.

Figure 2:
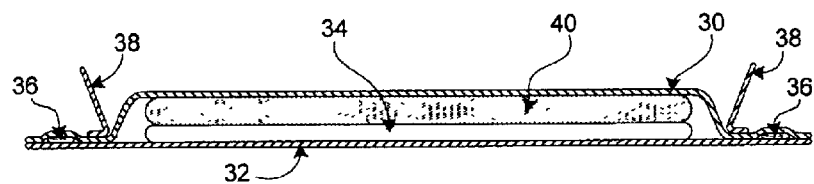
FIG. 2 is a side view of an absorbent article along line A—A of FIG. 1.

An absorbent core 34 (indicated by the dotted rectangular segment in FIG. 1) preferably is disposed between at least a portion of the topsheet 30 and backsheet 32. Preferably, the absorbent core 34 is disposed between at least a portion of the backsheet 32 and fluid handling layer 40. The preferred relative positions of the topsheet 30, backsheet 32, absorbent core 34 and fluid transfer layer 40 may be seen in FIG. 2, which is a cross-sectional view of the garment 10 of FIG. 1 as seen from reference line AA.

Preferred embodiments of the present invention may further comprise various additional features. One or more pairs of leg elastics 36 may extend adjacent the crotch edges 20. The garment 10 may also comprise one or more waste containment systems, such as a pair of standing leg gathers 38. The standing leg gathers 38 preferably extend longitudinally between the front region 12 and the rear region 14 along opposite sides of the garment's longitudinal axis 100.

The various parts of the garment 10 preferably are associated with one another to form a structure that preferably maintains its shape during the useful life of the garment 10. As used herein, the term "associated" encompasses configurations whereby a first part is directly joined to a second part by affixing the first part directly to the second part, by indirectly joining the first part to the second part through intermediate members, and by fixing the relative positions of various parts by capturing parts between other parts. Those skilled in the art will appreciate that various methods or combinations of methods may be used to securely join the parts of the garment 10.

The topsheet 30 and backsheet 32 may be constructed from a wide variety of materials known in the art. The invention is not intended to be limited to any specific materials for these components. The topsheet 30 and backsheet 32 can be shaped and sized according to the requirements of each of the various types of absorbent garment, or to accommodate various user sizes. In an embodiment of the invention in which the garment 10 is a diaper or an adult incontinence brief, the topsheet 30, backsheet 32, or both, may have an hourglass shape, as seen in FIG. 1, or may have a rectangular, trapezoidal, "T" shape, or other shape. In an embodiment of the invention in which the garment 10 is a feminine hygiene product, the topsheet 30, backsheet 32, or both, may have a rectangular or ovate shape, and may have tabs or "wings."

The backsheet 32 generally is made of any suitable pliable liquid impervious material known in the art or later discovered. Typical backsheet materials include films of polyethylene, polypropylene, polyester, nylon, and polyvinyl chloride and blends of these materials. For example, the backsheet 32 may be made of a polyethylene film having a thickness in the range of 0.02–0.04 mm. The backsheet 32 may be pigmented with, for example, titanium dioxide, calcium carbonate, and other white pigments, to provide the garment 10 with a pleasing color or to render the backsheet 32 opaque enough that exudates being contained by the garment 10 are not visible from outside the garment. In addition, backsheet 32 may be formed in such a manner that it is opaque, for example, by using various inert components in the polymeric film and then biaxially stretching the film. Other backsheet materials will be readily apparent to those skilled in the art. The backsheet 32 preferably should have sufficient liquid imperviousness to prevent any leakage of fluids through the backsheet 32. The required level of liquid imperviousness may vary between different locations on the garment 10.

The backsheet 32 may further comprise separate regions having different properties. In a preferred embodiment, portions of the backsheet 32 are air-permeable to improve the breathability, and therefore comfort, of the garment 10. The different regions may be formed by making the backsheet 32 of a composite of different sheet materials, chemical treatment, heat treatment, or other processes or methods known in the art. Some regions of the backsheet 32 may be fluid pervious. In one embodiment of the invention, the backsheet 32 is fluid impervious in the crotch 12, but is fluid pervious in portions of the front and rear regions 12, 14. The backsheet 32 may also be made from a laminate of overlaid sheets of material.

The backsheet 32 may be covered with a fibrous, nonwoven fabric such as is disclosed, for example, in U.S. Pat. No. 4,646,362 issued to Heran et al., which is hereby incorporated by reference in its entirety and in a manner consistent with the present application and invention. Materials for such a fibrous outer liner include a spun-bonded nonwoven web of synthetic fibers; a nonwoven web of cellulosic fibers, textile fibers, or a blend of cellulosic and textile fibers; a spun-bonded nonwoven web of synthetic fibers mixed with cellulosic, pulp fibers, or textile fibers; and melt blown thermoplastic fibers or mixtures of such thermoplastic fibers with cellulosic, pulp or textile fibers. These materials are well known and readily available in the art.

The moisture-pervious topsheet 30 may be made of any suitable relatively liquid-pervious material currently known in the art or later discovered that permits passage of a liquid there through. Examples of suitable topsheet materials include nonwoven spun-bonded or carded webs of polypropylene, polyethylene, nylon, polyester and blends of these materials, perforated, apertured, or reticulated films, and the like. Nonwoven materials are exemplary because such materials readily allow the passage of liquids to the underlying absorbent core 34.

The topsheet 30 preferably comprises a single-ply nonwoven material that may be made of carded fibers, either adhesively or thermally bonded, perforated or apertured film, spunbonded fibers, or water entangled fibers, which generally weigh from 0.3–0.7 oz./sq. yd. and have appropriate and effective machine direction and cross-machine (transverse) direction strength suitable for use as a topsheet material for the given application. The present invention is not intended to be limited to any particular material for the topsheet 30, and other topsheet materials will be readily apparent to those skilled in the art.

The topsheet 30 may further comprise several regions having different properties. In one embodiment of the present invention, the laterally distal portions of the topsheet 30 are preferably substantially fluid impervious and hydrophobic, while the remainder of the topsheet 30 is hydrophilic and fluid pervious. Different topsheet properties, such as fluid perviousness and hydrophobicity, may be imparted upon the topsheet 30 by treating the topsheet 30 with adhesives, surfactants, or other chemicals, using a composite of different materials, or by other means. Alternatively, the different properties can be achieved by making the topsheet from three separate components, a central, fluid pervious portion, and two lateral fluid impervious portions that can also serve to form standing leg gathers. Such a configuration is described in, for example, U.S. Pat. No. 6,068,620, the disclosure of which is incorporated by reference herein in its entirety. The topsheet 30 also may be made from a laminate of overlaid sheets of material. The topsheet 30 also may be treated in specific areas like the crotch region, with skin wellness ingredients like aloe and vitamin E.

As noted elsewhere herein, the topsheet 30 and backsheet 32 may be substantially coterminous, or they may have different shapes and sizes. The particular design of the topsheet and backsheet may be dictated by manufacturing considerations, cost considerations, and performance considerations. Preferably, the topsheet 30 is large enough to completely cover the absorbent core 34, and the backsheet 32 is large enough to prevent leakage from the garment 10. The design of topsheets 30 and backsheets 32 is known in the art, and a skilled artisan will be able to produce an appropriate topsheet 30 and an appropriate backsheet 32 without undue experimentation, using the guidelines provided herein.

The topsheet 30 and the backsheet 32 may be associated with one another using a variety of methods known in the art. For example, they may be thermally, ultrasonically, chemically, or thermal mechanically bonded to one another. They also may be joined using lines of hot melt adhesive or mechanical fasteners, such as thread, clips, or staples. In one embodiment, a hydrophilic adhesive, such as CYCLOFLEX™ as sold by National Starch, located in Bridgewater, N.J., is used to join the topsheet 30 to the backsheet 32. The particular joining method may be dictated by the types of materials selected for the topsheet 30 and backsheet 32.

An absorbent core 34 preferably is disposed between the topsheet 30 and the backsheet 32 in at least the crotch region 16. The absorbent core 34 may extend into either or both of the front and rear regions 12, 14. Although the absorbent core 34 depicted in FIG. 1 has a substantially rectangular shape (absorbent core 34 is outlined by dotted lines), other shapes may be used, such as a "T" shape, an hourglass shape, or the shape shown in FIG. 7. The shape of the absorbent core 34 may be selected to provide the greatest absorbency with a reduced amount of material. The absorbent core 34 may be associated with the topsheet 30, backsheet 32, or any other suitable part of the garment 10 by any method known in the art, in order to fix the absorbent core 34 in place.

The absorbent core 34 may be made from any suitable material or materials known in the art. Examples of suitable materials for use as the absorbent core 34 include creped cellulose wadding, absorbent foams, absorbent sponges, super absorbent polymers, absorbent gelling materials, fiberized cellulose, fluff pulp having tissue or synthetic materials between the absorbent core 34 and the topsheet 30 or any equivalent material or combination of materials. The size and capacity of the absorbent material should correspond to the application, for example, an incontinent brief for an adult may require a larger absorbent core than a diaper for a child. Zoned absorbency may also be used, if desired. For example, more absorbent capacity may be located in particular regions of the garment 10 depending on the gender of the intended wearer. The invention is not intended to be limited to any specific materials for use in the absorbent core 34.

In a preferred embodiment, the absorbent core 34 comprises super absorbent polymer distributed within a fibrous structure. Absorbent cores of this type are known in the art, and exemplary absorbent cores are described in U.S. Pat. Nos. 5,281,207, and 6,068,620 issued to Chmielewski et al., and U.S. Pat. No. 5,863,288, issued to Baker, the disclosures of which are herein incorporated by reference in their entirety.

Additional sublayers, transfer layers, acquisition layers, tissue wraps, and the like also may be incorporated into or otherwise associated with the absorbent core 34. Such layers may be provided to assist with transferring fluids to the absorbent core 34, handling fluid surges, preventing Rewet, containing absorbent material, improving core stability, or for other purposes. For example, a substantially rectangular, preferably nonwoven, sublayer (not shown), having a basis weight of about 0.1–2 oz., preferably about 0.4–0.6 oz., may overlay absorbent core 34. Those skilled in the art are capable of selecting materials, dimensions, and locations for such layers without undue experimentation.

A fluid handling layer 40 preferably is disposed between the topsheet 30 and the absorbent core 34. The fluid handling layer 40 preferably extends from the front region 12, through the crotch 16, and into the rear region 14, and it typically corresponds substantially to the shape of the absorbent core 34, and preferably is a little smaller. It is preferred that the fluid handling layer 40 be approximately the same width as, or narrower than, the absorbent core 34.

Any material can be used to manufacture the fluid handling layer 40, so long as it provides an absorbent article having the Strikethrough and Rewet values described herein. It is particularly preferred in the invention that the fluid handling layer 40 be comprised of at least one foam material, which preferably comprises a polymer. Any polymeric foam material effective in conferring to the absorbent article the physical Strikethrough and Rewet characteristics recited herein are suitable. Persons of skill in the art would readily be able to select and utilize such polymers to implement the present invention, based upon the guidance provided herein. Non-limiting exemplary polymers suitable in implementation of the present invention include polymers selected from the group consisting of polyurethanes, polyethylenes, polypropylenes, polyacrylics, polyamides, polyvinyl chlorides, epoxys, polystyrenes, melamine-formaldehyde polymers and combinations thereof. The foam-containing fluid handling layer 40 preferably comprises any suitable non-yellowing polymeric foam material, and most preferably is comprised of at least an aliphatic isocyanate-derived polyurethane foam. Other polymeric foams may be used together with the aliphatic isocyanate-derived polyurethane foam so long as the absorbent article maintains its desirable strikethrough and rewet properties.

Aliphatic isocyanate-derived polyurethane foams generally are known in the art. Skilled artisans are capable of making a suitable non-yellowing polyurethane foam using the guidelines provided herein. Given the desirable properties of the foam, a number of polymeric foam materials may be made in a variety of thicknesses. These materials then can be constructed into a fluid handling layer using the guidelines provided herein, and tested in accordance with the procedures outlined herein. Those polymeric foams, when constructed into an absorbent article and tested to have a third insult Strikethrough of less than about 45 seconds, and a third insult Rewet of less than about 35 grams, are useful polymeric foams in the present invention.

While not preferred in the present invention, it is possible to modify existing foam materials to be more hygienic and/or non-yellowing, and then use these foam materials in the invention, so long as the foams, when constructed into an absorbent article and tested to have a third insult Strikethrough of less than about 45 seconds, and a third insult Rewet of less than about 35 grams. For example, a conventional melamine-formaldehyde foam material available from BASF Corp., Research Triangle Park, N.C., designated BASOTECT®, has a formaldehyde content that typically is too high for use in a baby diaper. Such foams can be modified, however, to reduce the residual formaldehyde content, by, for example, using less formaldehyde or including a formaldehyde scavenger during production of the foam to thereby provide a foam more suitable for use in a baby diaper. Those skilled in the art are capable of modifying conventional melamine-formaldehyde foam materials to reduce the residual formaldehyde content, and then test the foam materials in accordance with the present invention to determine suitable foams for use herein.

It is preferred that the polymeric foam materials be comprised of an aliphatic isocyanate-derived polyurethane foam material, although such a foam material is not necessary for the invention. Aliphatic isocyanates are preferred starting materials due to the environmental hazards associated with using toluene or benzene-based isocyanates. In addition, aliphatic isocyanate-derived polyurethane foams do not yellow like other polyurethane foams, thereby making their use in a wearable absorbent article more desirable. Aromatic isocyanates can be used, however, to the extent the user is not concerned with yellowing or other disadvantages that may or may not result from their use.

Suitable aliphatic isocyanate-derived polyurethane foam materials can be made by using a prepolymerization process, or by directly polymerizing an aliphatic isocyanate with a polyol, in the presence of a catalyst and optionally water. It generally is preferred to form a prepolymer adduct having terminal isocyanate groups.

Suitable aliphatic polyisocyanates used to prepare the isocyanate-terminated prepolymer that may be employed in this invention may be either a compound composed only of an aliphatic chain or an alicyclic compound or a compound with an aromatic ring present in an aliphatic chain. Concrete examples thereof are hexamethylene diisocyanate, hexamethylene triisocyanate, bicycloheptane triisocyanate, undecanetriisocyanate, lysine ester triisocyanate, isophorone diisocyanate, dicyclohexylmethane diisocyanate, methylcyclohexane diisocyanate, dimethylcyclohexane diisocyanate, xylylene diisocyanate, tetramethylxylylene diisocyanate, their dimers, and their trimers. Of these, hexamethylene diisocyanate is especially preferable.

In accordance with the present invention, the aliphatic polyisocyanate component generally is in the form of an NCO prepolymer or a polyisocyanate adduct, more preferably a polyisocyanate adduct. Suitable polyisocyanate adducts for the present invention may be based, for example, on organic aliphatic diisocyanates including, for example, 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3- and -1,4-diisocyanate, 1-isocyanato-2-isocyanatomethyl cyclopentane, 1-isocyanato-3-isocyanatomethyl-3,5,5-trimethyl-cyclohexane (isophorone diisocyanate or IPDI), bis-(4-isocyanatocyclohexyl) methane, 2,4'-dicyclohexylmethane diisocyanate, 1,3- and 1,4-bis-(isocyanatomethyl)-cyclohexane, bis-(4-isocyanato-3-methylcyclohexyl)methane, $\alpha,\alpha,\alpha',\alpha'$-tetramethyl-1,3- and/or -1,4-xylylene diisocyanate, 1-isocyanato-1-methyl-4 (3)-isocyanatomethyl cyclohexane, 2,4- and/or ,6-hexahydrotoluylene diisocyanate, and mixtures thereof. It is preferred that the isocyanate be based on 1,6-hexamethylene diisocyanate. These and other suitable aliphatic isocyanates are described in, for example, U.S. Pat. Nos., 5,147,897, 5,164,421, 5,502,147, and WO 01/55242, the disclosures of which are incorporated by reference herein in their entirety.

Suitable polyisocyanate adducts containing biuret groups include polyisocyanates such as those described, for example, in U.S. Pat. Nos. 3,124,605, 3,358,010, 3,644,490, 3,862,973, 3,906,126, 3,903,127, 4,051,165, 4,147,714, and 4,220,749, the disclosures of which are herein incorporated by reference in their entirety. As set forth in these patents, these biuret group-containing polyisocyanates may be prepared by using co-reactants such as water, tertiary alcohols, primary and secondary monoamines, and primary and/or secondary diamines. These polyisocyanates preferably have an NCO content of 18 to 22% by weight and an average NCO functionality of 2.3 to 4.0, preferably of 3 to 3.5.

Suitable polyisocyanates containing isocyanurate groups include compounds such as those described, for example, in U.S. Pat. Nos. 4,288,586 and 4,324,879, the disclosures of which are herein incorporated by reference in their entirety; European Patents 3,765, 10,589 and 47,452, the disclosures of which are herein incorporated by reference; and German Offenlegungsschrifien 2,616,416, herein incorporated by reference. The isocyanato-isocyanurates generally have an average NCO functionality of 2.3 to 4.0, preferably of 3 to 3.5, and an NCO content of 5 to 30%, preferably 10 to 25% and most preferably 15 to 25% by weight.

Uretdione diisocyanates may be prepared by oligomerizing a portion of the isocyanate groups of a diisocyanate in the presence of a trialkyl phosphine catalyst, and may be used in admixture with other aliphatic and/or cycloaliphatic polyisocyanates, particularly the isocyanurate group-containing polyisocyanates described hereinabove.

Urethane group-containing polyisocyanates which may be prepared in accordance with the process disclosed in U.S. Pat. No. 3,183,112, herein incorporated by reference in its entirety, by reacting excess quantities of polyisocyanates, preferably diisocyanates, with low molecular weight glycols and polyols having molecular weights of less than 400, such as trimethylol propane, glycerine, 1,2-dihydroxy propane and mixtures thereof, also are useful in the present invention.

Allophanate group-containing polyisocyanates include, for example, those prepared according to the processes disclosed in U.S. Pat. Nos. 3,769,318, 4,160,080 and 4,177, 342, the disclosures of which are herein incorporated by reference. Isocyanurate and allophanate group-containing polyisocyanates include, for example, those which may be prepared in accordance with the processes set forth in U.S. Pat. Nos. 5,124,427, 5,208,334 and 5,235,018; the disclosures of which are herein incorporated by reference. These polyisocyanates containing isocyanurate and allophanate groups preferably have an NCO content of 16 to 22% by weight, most preferably of 18 to 21% by weight.

Suitable carbodiimide group-containing and uretone imine group-containing polyisocyanates for use in the present invention include, for example, those that may be prepared by oligomerizing di- or polyisocyanates in the presence of known carbodiimidization catalysts such as described in, for example, German Patentschrifien 1,092, 007, herein incorporated by reference, U.S. Pat. No. 3,152, 162, herein incorporated by reference, and German Offenlegunschrifien 2,504,400, 2,537,685 and 2,552,350, the disclosures of which are herein incorporated by reference.

The aforementioned isocyanates are preferably reacted with a polyol to prepare the polyurethane foam material in the present invention. Any suitable polyol can be used so long as the ultimate foam produces an absorbent article having the properties described herein. A suitable polyol employed to form a prepolymer using the aliphatic polyisocyanate, is a polyol having a number average molecular weight of 100 to 5,000, preferably 200 to 3,000, and containing on the average 2 to 3 functional groups. Examples of the polyol useful in this invention include polyether polyols such as adducts [e.g., polyethylene oxide, polypropylene oxide, and poly(ethylene oxide-propylene oxide) copolymer] of dihydric or trihydric alcohols (e.g., ethylene glycol, propylene glycol, glycerol, hexanetriol, and triethanolamine) and alkylene oxides (e.g., ethylene oxide, propylene oxide, and butylene oxide), and polytetramethylene ether glycol obtained by subjecting tetrahydrofuran to ring opening polymerization; lactone-type polyester polyols obtained by adding lactons such as caprolactone, glycolide and lactide to the above dihydric or trihydric alcohols via ring opening; compounds obtained by condensing the above dihydric or trihydric alcohols with hydroxycarbonic acids such as glycolic acid, lactic acid, and salicylic acid; compounds obtained by condensing dicarboxylic acids such as oxalic acid, maric acid, succinic acid, glutaric acid, phthalic acid, and adipic acid with diols such as ethylene glycol, and propylene glycol; and condensed polyester polyols obtained by adding acid anhydrides such as phthalic anhydride with diols.

The prepolymer can be prepared from the aliphatic polyisocyanate and the polyol in a known manner by the addition reaction of the respective components. Regarding the reaction ratio of the polyisocyanate and the polyol at that time, an NCO/OH ratio of about 1.4 to 2.6, preferably from about 1.5 to 2.5 is used.

A prepolymer having the isocyanate groups in substantially all the molecule terminals can be made from the above described reactions. The prepolymer then preferably is reacted with water in the presence of the hardening catalyst. The hardening reaction proceeds by chain extension accompanying a urea bond that occurs by reacting an amino group resulting from the reaction of the terminal isocyanate group of the prepolymer and water with the terminal isocyanate group of the other prepolymer.

The amount of water used in the reaction can be anywhere from about 0.4 to 5 times, preferably 0.5 to 4.5 times the isocyanate equivalent of the prepolymer. In accordance with one aspect of this invention in which the polyurethane urea foam is formed by the reaction of the isocyanate-terminated prepolymer and water, it has been found that the reaction can of course be carried out by using a highly active hardening catalyst such as amines or organometallic compounds. Even when one employs carboxylic acid metal salts of low toxicity, the hardening reaction rapidly proceeds, and a less toxic non-yellowing polyurethane foam can be prepared. Those skilled in the art will appreciate that the same hardening reaction can take place without forming the aforementioned prepolymer, and skilled artisans are capable of making a suitable foam for use in the present invention using the guidelines provided herein.

Examples of suitable carboxylic acid metal salts useful as an active hardening catalyst include alkali metal salts, lead salts, alkaline earth metal salts, especially calcium salts, of aliphatic carboxylic acids which are $C_2$–$C_{10}$ alkane acids such as acetic acid, propionic acid, butyric acid, valeic acid, caproic acid, caprylic acid, capric acid, and 2-ethylhexanoic acid. Of these, the calcium or sodium salts are preferable. The amount of the carboxylic acid metal salt can be 0.1 to 5 parts by weight, preferably 1 to 3 parts by weight per 100 parts by weight of the prepolymer.

The polyurethane foam useful in the invention also may be formed by the reaction of the isocyanate-terminated prepolymer and water in the presence of an amine-type catalyst. The amine-type catalyst can be an amine-type catalyst well known in the urethane field; a tertiary amine is especially preferable. Examples of suitable tertiary amine include monoamines such as triethylamine, and dimethyl cyclohexylamine; diamines such as tetramethylethylenediamine, and tetramethylhexanediamine; triamines such as tetramethylguanidine; cyclic amines such as triethylenediamine, dimethylpiperadine, and methylmorphorine; alcoholamines such as dimethylaminoethanol, trimethylaminoethylethanolamine, and hydroxyethylmorphorine; ether amines such as bisdimethylaminoethyl ethanol; diazabicycloalkenes such as 1,5-diazabicyclo(5,4,0)undecene-7 (DBU), and 1,5-diazabicyclo(4,3,0)nonene-5; and organic acid salts of the diazabicycloalkenes such as phenol salt, 2-ethylhexanoate and formate of DBU. Of these, a diazabicycloalkene such as that disclosed in U.S. Pat. No. 5,147,897, and a salt of it and an organic acid are especially preferable. These amines can be used either singly or in combination.

The amine-type catalyst can be used in an amount of usually 0.1 to 10 parts by weight, more preferably 0.4 to 4 parts by weight.

It is possible in the invention, that two or more prepolymers different in isocyanate portion and/or polyol portion may be mixed and used, or the aforesaid polyol having the average molecular weight of 100 to 5,000 and containing on the average 2 to 3 functional groups may be added to the hardening reaction system, as required. This enables modification of a viscosity of an expansion starting solution composed of a prepolymer, water, a catalyst, etc., increase in compatibility thereof and control of properties of the hardened product. Even in the method of this invention that conducts the chain extension chiefly by the formation of the urea bond via the reaction of the isocyanate group and water, the polyol can be incorporated into the hardened product by the formation of the urethane bond via the reaction of the hydroxyl group and the isocyanate group. The amount of the polyol can be usually 60% or less, preferably 50% or less.

A particularly preferred method of making an aliphatic isocyanate-derived polyurethane foam for use in the invention is described in WO 01/55242, the disclosure of which is incorporated by reference herein in its entirety. A flexible, semi rigid or rigid, preferably open-celled polyurethane foam preferably is made using at least one complexing agent selected from ethylenimine, polyethylenimine, polyvinylamine, carboxy-methylated polyethylenimines, phosphono-methylated polyethylenimines, quaternized polyethylenimines and/or dithiocarbamitized polyethylenimines.

Examples of suitable complexing agents are: ethylenimine, polyethylenimines having a molecular weight range from 500 to 30,000 g/mol, carboxy-methylated polyethylenimines having a molecular weight range from 1000 to 50,000 g/mol, phosphono-methylated polyethylenimines having a molecular weight range from 1000 to 50,000 g/mol, quaternized polyethylenimines having a molecular weight range from 1000 to 50,000 g/mol, dithiocarbamitized polyethylenimines having a molecular weight range from 1000 to 50,000 g/mol, and polyvinylamines.

These particularly preferred complexing agents can be applied to the polyurethane foam by two different methods. Firstly, the production of the polyurethane foam by reaction of polyisocyanates with compounds having at least two hydrogen atoms which are reactive toward isocyanates can be carried out in the presence of the complexing agent. However, the complexing agents also can be reacted with isocyanate to form prepolymers, i.e. reaction products of the complexing agents and polyisocyanates which have free isocyanate groups at the end of the chain. Prepolymers and pseudoprepolymers and their preparation are generally known and have been described above.

A second method is to impregnate the polyurethane foam with the complexing agent after production of the foam. Treatment of the foam with a liquid complexing agent or a solution of the solid or liquid complexing agent in a suitable solvent is believed to result in the foam being impregnated with the complexing agent. Suitable solvents include protic solvents, for example water, acetone, i-propanol or methyl ethyl ketone, or haloalkanes such as 1,2-dichloromethane. The solvent can subsequently be removed from the foam impregnated with the complexing agent. This can be achieved by simple application of a vacuum or by drying at up to 50° C. Thermal treatment at from 50 to 150° C. for from 4 to 72 hours enables the complexing agents to react with the foam and thus be covalently bound to it.

To achieve better immobilization of the complexing agent, the foam can be produced using an excess of isocyanate. In this case, the complexing agent can be fixed to the foam framework via remaining isocyanate groups.

The foam also can be impregnated beforehand with a dilute isocyanate solution. The foam which has been prepared in this way then may be impregnated with the solution of complexing agent. Here too, the complexing agent can be bound to the foam via the isocyanate groups.

In a post-impregnation of the foams with a solution of complexing agent, the absorption capacity of the foam also is dependent on the type and polarity of the solvent in which the active compound has been dissolved. Specifically using acetone as the preferred solvent for the complexing agent, increases the capacity of the foam for the complexing agent.

The complexing agents applied to the foam by impregnation can, if desired, be crosslinked on the foam in a further step. Examples of suitable crosslinkers include nonvolatile PEC bisglycidyl ethers or comparable functional compounds, or polycarboxylic acids. The temperatures required for crosslinking are typically around 80° C. for most cross-linking, and from about 120 to about 130° C. for the polycarboxylic acids.

The polyurethane foams that are particularly useful in the present invention contain anywhere from about 0.1 to about 50% by weight of the aforementioned complexing agent, based on the weight of the foam.

It is advantageous to make the polyurethane foams hydrophilic, as a result of which the foam can be wetted with a liquid, such as urine, and the like. The hydrophilicity of the polyurethane foams can be increased, for example, by use of polyetherols having a high ethylene oxide content in the chain.

The production of polyurethane foams by reacting isocyanates, for example polyisocyanates, with compounds having at least two hydrogen atoms which are reactive toward isocyanates is generally known. To produce the polyurethanes of the present invention, the isocyanates can be reacted with the compounds having at least two active hydrogen atoms in the presence of blowing agents and, if desired, catalysts and/or auxiliaries and/or additives. Here, the compounds having at least two hydrogen atoms that are reactive toward isocyanate groups and the above mentioned blowing agents, catalysts and auxiliaries and/or additives frequently are combined to form a polyol component before the reaction, and this is then brought into contact with the isocyanate component.

The particularly preferred starting materials that are possible for carrying out the process of the present invention, i.e. the isocyanates, the compounds having at least two active hydrogen atoms, the blowing agents and, if desired, the catalysts and/or the auxiliaries and/or additives, are as follows:

As isocyanates, preferably polyisocyanates, particularly preferably diisocyanates, most preferably organic diisocyanates, it is possible to use the customary and known (cyclo)aliphatic and aromatic polyisocyanates. Examples of aromatic polyisocyanates are toluylene 2,4 and 2,6-diisocyanate (TDI), diphenylmethane 4,4'-, 2,4'- and 2,2'-diisocyanate (MDI), polyphenylene-polymethylene polyicocyanatos (crude MDI), and naphthylene 1.5-diisocyanate.

Examples of (cyclo)aliphatic diisocyanates or triisocyanates are tetramethylene 1,4-diisocyanate, hexamethylene 1,6-diisocyanate, isophorone diisocyanate, 2 methylpentamethylene diisocyanate, 2,2,4- or 2,4,4-trimethylhexamethylene 1,6-diisocyanate, 2-butyl-2-ethylpentamethylene diisocyanate, 1,4-diisocyanatocyclohexane, 3-isocyanatomethyl-1-methyl 1-isocyanatocyclohexane, isocyanatopropylcyclohexyl isocyanate, xylylene diisocyanate, tetramethylxylylene diisocyanate, bis(4-isocyanatocyclohexyl) methane, lysine ester isocyanates, 1,3- or 1,4-bis(isocyanatomethyl) cyclohexane, 4-isocyanatomethyloctamethylene 1,8 diicocyanate and mixtures thereof or the oligoisocyanates or polyisocyanates prepared therefrom.

While the aforementioned aromatic and cycloaliphatic isocyanates may be used to make suitable foams, it is preferred not to use them for use in an absorbent garment to be used by an infant, since consumers typically perceive their use to be hazardous, regardless of whether the final product is hazardous or not. It is particularly preferred in the invention to use the aliphatic isocyanates selected from tetramethylene 1,4-diisocyanate, hexamethylene 1,6-diisocyanate, isophorone diisocyanate, 2 methylpentamethylene diisocyanate, 2,2,4- or 2,4,4-trimethylhexamethylene 1,6-diisocyanate, 2-butyl-2-ethylpentamethylene diisocyanate, and mixtures thereof or the oligoisocyanates or polyisocyanates prepared therefrom The oligoisocyanates or polyisocyanates can be prepared from the above-mentioned diisocyanates or triisocyanates or mixtures thereof by coupling by means of urethane, allophanate, urea, biuret, uretdione, amida, isocyanurate, carbodiimide, uretonimine, oxadiazinetrione or iminooxadiazinedione structures.

The isocyanates mentioned above also can be modified, for example by incorporation of carbodiimide groups. The polyisocyanates are also frequently used in the form of prepolymers. These are reaction products of the polyisocyanates mentioned under with polyol components. Use is usually made of isocyanate prepolymers, i.e. reaction products of polyols and polyisocyanates which have free isocyanate groups at the end of the chain. The prepolymers and pseudoprepolymers and their preparation are generally known and have been described many times. In the process of the present invention, particular preference is given to using prepolymers having an NCO content in the range from about 3.5 to about 25% by weight.

In a preferred embodiment of the process of the present invention, biuretic, isocyanurates and allophanates based on aliphatic isocyanates are used as the isocyanate component.

Any compounds having at least two active hydrogen atoms can be used in the invention. Preferred compounds include polyester alcohols and particularly preferred are polyetherols having a functionality of from 2 to 8, in particular from 2 to 4, preferably from 2 to 3, and a molecular weight in the range from 1000 to 8500 g/mol, preferably from 1000 to 6000. The compounds having at least two active hydrogen atoms also include chain extenders and cross linkers that may be additionally used, if desired. Chain extenders and cross linkers are preferably 2- and 3-functional alcohols having molecular weights of less than 1000 g/mol, in particular in the range from 60 to 150. Examples include ethylene glycol, propylene glycol, diethylene glycol, dipropylene glycol, polyethylene glycol having a molecular weight of less than 1000, polypropylene glycol having a molecular weight of less than 1000 and/or 1,4 butanediol. Diamines also can be used as cross linkers. If chain extenders and cross linkers are used, their amount is preferably up to 5% by weight, based on the weight of the isocyanates.

It is possible in the invention to use any of the known and customary polyurethane formation catalysts as catalysts for producing the polyurethane foams of the present invention. For example organic tin compounds such as tin diacetate, tin dioctoate, dialkyltin dilaurate, and/or strongly basic amines such as triethylamine, pentamethyldiethylenetriamine, bis (dimethylaminoethyl) ether, 1,2-dimethylimidazole, dimethylcyclohexylamine, dimethylbenzylamine or preferably triethylenediamine are used. The catalysts are preferably used in an amount of from 0.01 to 5% by weight, preferably from 0.05 to 2% by weight, based on the weight of the isocyanates.

It is preferred to use water as a blowing agent for producing the polyurethane foams, because the water reacts with the isocyanate groups to liberate carbon dioxide. Together with or in place of water, it is also possible to use physically acting blowing agents, for example hydrocarbons such as n-pentane, isopentane or cyclopentane or halogenated hydrocarbons such as tetrafluoroethane, pentafluoropropane, heptafluoropropane, pentafluorobutane, hexafluorobutane or dichloromonofluoroethane, or acetals such as methylal. The amount of physical blowing agent is preferably in the range from 1 to 15% by weight, in particular from 1 to 10% by weight, and the amount of water is preferably in the range from 0.5 to 10% by weight, in particular from 1 to 5% by weight, based on the weight of the compounds having at least two active hydrogen atoms.

In the production of the polyurethane foams of the present invention, the polyisocyanates and the compounds having at least two hydrogen atoms that are reactive toward isocyanate groups are preferably reacted in such amounts that the equivalence ratio of isocyanate groups to the sum of the active hydrogen atoms is 0.7–1.8:1, preferably 0.7–1.20:1.

The polyurethane foams preferably are produced by the one-shot method, for example with the aid of the high-pressure or low-pressure technique. The foams can be produced in open or closed metallic molds or by continuous application of the reaction mixture to conveyor belts for producing foam blocks.

It is particularly advantageous to employ the two-component process in which, as indicated above, a polyol component and an isocyanate component are prepared and foamed with one another. The components preferably are mixed at from 15 to 90° C., preferably from 20 to 60° C. and particularly preferably from 20 to 35° C., and introduced into a mold or applied to a conveyor belt. The temperature in the mold usually is in the range from 20 to 110° C., preferably from 30 to 60° C. and particularly preferably from 35 to 55° C.

In the direct addition of the complexing agent during the production of the polyurethane foams, the complexing agent can be added to either the polyol component or the isocyanate component. Preference is given to adding the complexing agent to the polyol component.

In the method of this invention, additives such as surface active substances, foam stabilizers, cell regulators, blowing agents, fire retardants, chain extenders, crosslinking agents, external and internal mold release agents, fillers, pigments, hydrolysis inhibitors, and fungistatic and bacteriostatic substances may be added as is often the case with production of ordinary polyurethanes. Moreover, in order to react the remaining isocyanate groups left after expansion, the foam may be heated to conduct post-hardening.

Particularly preferred components used to prepare the foams of the present invention are the aliphatic isocyanates and oligomers thereof, MDI available under the tradename LUPRANAT®, BASF Aktiengesellschaft, Ludwigshafen, Germany, polyetherols available under the tradename LUPRANOL®, BASF Aktiengesellschaft, Ludwigshafen, Germany, catalysts such as bis(dimethylaminoethyl)ether, available under the tradename LUPRAGEN®, BASF Aktiengesellschaft, Ludwigshafen, Germany, polyethylenimines as complexing agents, available under the tradename LUPASOL®, BASF Aktiengesellschaft, Ludwigshafen, Germany, aminopropylimindazol, tetramethylhexamethylene diamine, as well as suitable surfactants, stabilizers and other conventional additives.

The physical characteristics of the absorbent article of the invention (e.g., Strikethrough and Rewet) can be affected by a variety of physical properties of the foam used in accordance with an implementation of the present invention. These properties include the density of the foam, sink time, up take, tensile strength, cell size (A), cell size (B), hole size, and change in basis weight. The change in basis weight of the foam materials is, in essence, a measure of the solubles content of the foam. The more solubles present in the foam material, the greater the change in basis weight. These factors also influence the cost effectiveness of the absorbent articles.

Foam density in grams of foam per liter of foam volume in air is specified herein on a dry basis. Thus, the amount of absorbed aqueous liquid, e.g., that residual liquid which may be left in the foam, is disregarded in calculating and expressing foam density. Foam density as specified herein does include, however, residual solid material such as electrolyte, emulsifiers, hydrophilizing agents, and the like, in the polymerized foam. Such residual material may, in fact, contribute significant mass to the foam material. Persons of ordinary skill in the art would readily be able to use a variety of conventional techniques to produce foams in accordance with an implementation of the present invention.

Any suitable procedure that will provide a determination of mass of solid foam material per unit volume of foam structure can be used to measure foam density. For those situations where the foam sample preparation procedures (drying, aging, preflexing, etc.,) might inadvertently alter the density measurements obtained, then alternate density determination tests may also be utilized. Such alternative methods, for example, might include gravimetric density measurements using a test liquid absorbed within the foam material. This type of density determination method can be useful for characterizing very low density foams such as the foams herein wherein the dry density approximates the inverse of the pore volume of the foam. See Chatterjee, "Absorbency," Textile Science and Technology, Vol. 7, 1985, p. 41. The ranges for foam density set forth herein are intended to be inclusive, i.e., they are intended to encompass density values that may be determined by any reasonable experimental test method.

The foam materials useful in the fluid handling layer 40 of the present invention will preferably have dry basis density values of from about 10 to about 800 g/l, particularly preferably from about 20 to about 700 g/l, more preferably from about 50 to about 95 g/l, and most preferably from about 55 to about 85 g/l. The density of the foam materials of the invention can be adjusted to within the foregoing ranges by controlling some of the foam composition and processing parameters, as will be readily apparent to those skilled in the art. Density of the foam may be uniform throughout the structure or non-uniform. Some portions or zones of the foam structure may have relatively higher or lower densities than other portions or zones thereof.

The thickness of the foam-containing fluid handling layer 40 also may affect the Strikethrough and Rewet properties of the absorbent article. In addition, the thickness of the foam-containing fluid handling layer also has an affect on the overall comfort and feel of the garment. The fluid handling layer 40 may have a uniform uncompressed thickness, or it may be constructed with a non-uniform thickness in order to provide localized thicker or thinner regions that may provide specific benefits to particular areas of the garment 10. In one embodiment, the foam-containing fluid handling layer 40 has a uniform uncompressed thickness of between about 0.1 millimeters and about 10 millimeters. In a more preferred embodiment, the foam-containing fluid handling layer 40 has a uniform uncompressed thickness of between about 1 millimeters and about 5 millimeters. In a most preferred embodiment, the foam-containing fluid handling layer 40 has a uniform uncompressed thickness of about 1.5 millimeters to about 4.5 millimeters. The uncompressed thickness refers to the thickness of the foam-containing fluid handling layer 40 in its fully relaxed state, prior to being assembled into the garment 10.

Skilled artisan will appreciate that the preferred thickness for the fluid handling layer 40 foam material may vary depending on the particular size of absorbent garment, and its intended use. That is, the thickness can be determined or varied depending on the desired capacity of the foam. For example, for larger babies and adults, a higher capacity material typically is needed. Those skilled in the art are capable of determining the suitable thickness for the foam material useful in forming the fluid handling layer 40, using the guidelines provided herein.

The dry foam basis weight (in g/m$^2$) and the foam basis weight after being washed (in g/m$^2$) also may affect the Strikethrough and Rewet properties of the absorbent article. It is preferred that the foam materials used in the invention have a dry foam basis weight within the range of from about 100 to about 350, preferably within the range of from about 175 to about 300, and most preferably within the range of from about 200 to about 300 g/m$^2$. It is preferred that the foam materials used in the invention have a foam basis weight after washing within the range of from about 100 to about 350, preferably within the range of from about 175 to about 300, and most preferably within the range of from about 200 to about 300 g/m$^2$. The dry foam basis weight and the foam basis weight after being washed can be determined using techniques well known in the art.

The change in basis weight (absolute value of the foam basis weight after washing minus the dry foam basis weight) preferably ranges anywhere from about 1 to about 100, preferably from about 2 to about 75, and more preferably from about 2 to about 70. It is even more preferred in the invention that the change in basis weight (absolute value) be less than 20, and most preferred that the change in basis weight be less than 15.

The sink time (seconds), which is a measure of the acquisition rate, also may affect the Strikethrough and Rewet properties of the absorbent article. It is preferred that the foam materials used in the invention have a sink time within the range of from about 1 to about 100 seconds, preferably from about 2 to about 90 seconds, and more preferably from about 2 to about 50 seconds. It is preferred that the foam materials used in the invention have a sink time after washing within the range of from about 0.5 to about 80 seconds, preferably from about 0.75 to about 70 seconds, and more preferably from about 0.6 to about 60 seconds. Sink time for the foam materials useful in fluid handling layer can be determined using techniques well known in the art.

A method used to determine sink time and weight up-take in the present invention is to condition the foam samples for about 24 hours at ambient temperature and relative humidity. Samples of the foam then are cut into 3×3×3 cm$^3$ and laid on the surface of deionized water. The sample is weighed prior to dropping on the surface of deionized water. The time it takes for the top surface of the sample cube to be substantially wet with water is the sink time. The wet foam samples then are weighed. The difference in weight is the weight up-take. It is preferred in the present invention that the foam have a weight up-take within the range of from about 5 to about 50 grams, more preferably from about 10 to about 30 grams, and most preferably from about 15 to about 25 grams.

Foam cell size also may be useful in defining preferred foam materials of this invention. The foam cell size can be determined from the top of the foam sample (cell size A), or from the side of the sample (cell size B). Foam cells will frequently be non-spherical in shape. The size or "diameter" of such cells is another commonly utilized parameter for characterizing foams in general as well as for characterizing certain preferred absorbent foams of the type utilized in the present invention. Since cells in a given sample of polymeric foam will not necessarily be of approximately the same size, an average cell size, i.e., average cell diameter, will often be specified.

Cell size, like foam density, foam thickness, change in basis weight, and drop time, can also impact on the characteristics of the foam, in accordance with an implementation of the present invention. Since cell size is a factor that can affect the capillarity of the foam, cell size is a foam structure parameter that can directly affect both the fluid acquisition (e.g., Strikethrough) and the fluid retention (e.g., Rewet) properties of the absorbent articles described herein. Cell size can also affect mechanical properties of the foam absorbents herein including such features as flexibility and resiliency.

A number of techniques are available for determining average cell size in foams. These techniques include mercury porosimetry methods that are well known in the art. Another technique for determining cell size in foams involves simple photographic measurement of a foam sample. For example, a photomicrograph of a fracture surface of a typical polyurethane foam absorbent structure of the present invention can be taken. Superimposed on the photomicrograph is a scale representing a dimension of 10 microns. Such a scale can be used to determine average cell size via an image analysis procedure. Image analysis of photomicrographs of foam samples is, in fact, a commonly employed analytical tool that can be used to determine average cell size of the foam structures herein. Such a technique is described in greater detail in U.S. Pat. No. 4,788,225, issued to Edwards et al., which is incorporated herein by reference in its entirety. It is preferred in the invention to measure the cell size, both cell size A and cell size B by taking a statistical average from as many cells possible (preferably up to about 30) using raster electron microscopy (REM), and visualizing by the eye.

As indicated hereinbefore, the dimensions of cells in the absorbent foams of this invention will generally not be uniform so an average cell size for any given foam sample or zone in a foam sample can and should be calculated. It is, of course, possible to utilize absorbent foams which have discrete, identifiable zones of relatively larger or relatively smaller average cell size. It is preferred in the present invention that the cell size A be more than about 200 μm, preferably more than about 350 μm, and most preferably from about 400 to about 1,000 μm. It also is preferred that the cell size B be more than about 100 μm, more preferably, more than about 25 μm, and most preferably, from about 300 to about 550 μm.

Hole diameter, which is related to cell size A and cell size B, also may be a factor affecting the Strikethrough and Rewet properties of the absorbent garments of the invention, since it is believed to affect the fluid permeability of the foam material. The hole diameter can be measured in the same manner that the cell size A and cell size B are measured, with the exception that the hole diameter is the size of the holes connecting the cells. That is, the hole diameter can be ascertained by measuring the hole diameter of as many holes as possible (again, up to about 30) using REM, and visual inspection, in both the A and B directions (e.g., on the top of the sample, and across the thickness of the sample). It is preferred in the present invention that the hole diameter be greater than about 50 μm, more preferably greater than about 100 μm, and most preferably from about 125 to about 400 μm.

Another characteristic of the foam materials of the invention that has an impact on the Strikethrough and Rewet properties is the tensile strength of the foam. The tensile strength can be measured in accordance with any known method for measuring tensile strength of a foam material. Preferably, the tensile strength is measured in accordance with DIN EN ISO 1798, and is measured at two separate points on the foam sample, and then the value averaged. It is preferred that the foam materials used in making the fluid transfer layers of the invention have a tensile strength within the range of from about 1 to about 500 kPa, more preferably from about 25 to about 100 kPa, and most preferably from about 30 to about 75 kPa.

Persons of ordinary skill in the art are capable of varying the cell size, hole diameter, tensile strength, density, and other characteristics discussed herein to obtain foams in accordance with the present invention, using conventional materials and techniques. Further, various techniques and methods for measuring such characteristics are well known in the art. For example, various such techniques are described in U.S. Pat. No. 5,268,224, issued to DesMarais et al. on Dec. 7, 1993, which is incorporated herein by reference in its entirety.

Optionally, the foam additionally comprises a stabilizing agent. The stabilizing agent may be a crosslinking agent. Non-limiting exemplary stabilizing agents include formaldehyde, glutaraldehyde, glyoxal, glyoxylic acid, oxydisuccinic acid, citric acid, a dialdehyde having 2 to 8 carbon atoms, a monoaldehyde having an acid functionality and 2 to 8 carbon atoms, a polycarboxylic acid having 2 to 9 carbon atoms, and combinations thereof. The stabilizing agent is preferably selected from the group consisting of formaldehyde, glutaraldehyde, glyoxal, glyoxylic acid, oxydisuccinic acid, citric acid and combinations thereof. When the stabilizing agent is a crosslinking agent, the crosslinking agent may be selected from the group consisting of a dialdehyde having 2 to 8 carbon atoms, a monoaldehyde having an acid functionality and 2 to 8 carbon atoms, a polycarboxylic acid having 2 to 9 carbon atoms, and combinations thereof. Most preferred stabilizing agents are silicon containing stabilizing agents available under the tradename TEGOSTAB®, Goldschmidt, a division of Degussa, Essen, Germany, and more preferably, TEGOSTAB® B 8418.

The foam material that preferably is included in fluid handling layer 40 may additionally comprise a surfactant, a filler, an additive or a combination thereof. Preferably, the additive is selected from the group consisting of surfactants, flame retardants, reinforcing agents, auxiliary blowing agents, medicaments, fragrances, colorants, cleaners, abrasives and combinations thereof.

The fluid handling layer 40 may be formed in a variety of ways and the inventions is not intended to be limited to any specific manner of formation. If the fluid handling layer 40 is comprised of a foam material, it preferably is thermo-formed. Even more preferably, the fluid handling layer 40 is thermo-bonded to the substantially impermeable backsheet 32 or the permeable topsheet 30.

The fluid handling layer 40 may include a foam having an open cell or closed cell structure. The fluid handling layer 40 may extend to the longitudinally distal edges 18 of the garment 10, but preferably, it extends only so far as, more preferably, a little less than, the longitudinal dimension of the absorbent core 34. If fluid handling layer 40 extends to the longitudinal distal edges 18 of the garment, the portions of the fluid handling layer 40 proximal to the longitudinally distal edges 18 may improve the fit, comfort, and leakage resistance of such articles. These portions of the fluid handling 40 may also reduce the likelihood that the edge of the garment will double over on itself, or "roll over," by providing rigidity to the edge of the garment.

In a preferred embodiment, the fluid handling layer 40 is associated with the garment 10 in the front and rear regions 12, 14, such the garment 10 tends to contract around the wearer's body when the fluid handling layer 40 elastically contracts, presuming that the fluid handling layer 40 is associated with the other components of the garment while in the stretched state. Preferably, the foam-containing fluid handling layer 40 provides a lateral contracting force to the front and rear regions 12, 14, but not to the crotch region 16. In one embodiment, the portions of the foam-containing fluid handling layer 40 in both the front and rear regions 12, 14 are stretched along the lateral axis 102 prior to being associated with the garment 10. In this embodiment, the fluid handling layer 40 then is attached to the garment 10 in the front and rear regions 12, 14 in this extended state. Preferably, the fluid handling layer 40 is attached to one or both of the topsheet 30 and the backsheet 32, however, the fluid handling layer 40 may be attached to any suitable part of the garment 10 located in the front and rear regions 12, 14, or in the crotch region 16.

In this particular embodiment of the invention, when the fluid handling layer 40 is allowed to contract, the restoring force contracts the garment 10 around a wearer's waist. The portion of the foam-containing fluid handling layer 40 that resides in the crotch region 16 preferably is not directly joined to the garment 10, or is joined to the garment 10 while it is contracted, so that this part of the fluid handling layer 40 is in a relaxed or contracted state during use. In another embodiment, the fluid handling layer 40 may comprise a heat-activated elastic material that is attached to the garment 10 in the relaxed state, then heat activated to cause it to elastically contract. Such a materials is disclosed in U.S. Pat. No. 4,640,859, issued to Hansen et al., the disclosure of which is incorporated herein by reference in its entirety.

In one embodiment, that may be appropriate as an infant's diaper, the foam-containing fluid handling layer 40 is between about 3 inches and about 6 inches wide (i.e., 3 to 6 inches in the lateral dimension 102). In this embodiment, the longitudinal ends of the fluid handling layer 40 may be stretched along the lateral axis 102 to between about 50% to about 150% more than their original width before being secured to the garment 10. More preferably, the longitudinal ends of the fluid handling layer 40 may be stretched along the lateral axis 102 to be more than between about 75% to about 125% of their original width before being secured to the garment 10. Most preferably, the longitudinal ends of the fluid handling layer 40 are stretched along the lateral axis 102 to be more than about 100% of their original width before being secured to the garment 10. It is even more preferred, however, that fluid handling layer 40 not be stretched before being secured to the garment.

Wider garments 10, such as those intended for use by adults, may benefit from a wider fluid handling layer 40. In addition, the fluid handling layer 40 may be provided with a greater or lesser amount of stretch prior to being secured to the garment 10, depending on whether the application requires a greater or lesser contracting force, respectively. Those skilled in the art are capable of stretching, or preferably not stretching, the various portions of the foam-containing fluid handling layer 40, and using various sizes and types of fluid handling layers 40, using the guidelines provided herein.

Generally, the fluid handling layer 40 is narrower than the topsheet 30 and backsheet 32 so that it is fully contained between the topsheet 30 and backsheet 32. The width of the fluid handling layer 40 in the crotch region 16 may be established so that it does not cause bunching of the garment between the wearer's legs, and does not increase the rigidity of the crotch edges 20, which may cause discomfort and leakage. The width of the foam-containing fluid handling layer 40 in the front and rear regions 12, 14 may be selected to provide improved fit, comfort and leakage protection. In one embodiment, the fluid handling layer 40 may extend to the lateral edges 28 of the topsheet 30 or backsheet 32 in one or both of the front and rear regions 12, 14. It is most preferred, that fluid handling layer 40 extend laterally the same as, or slightly less than, the amount absorbent core 34 extends laterally.

The fluid handling layer 40 may be attached to the garment 10 by any suitable method known in the art. Exemplary bonding methods include using hot melt adhesives, ultrasonic bonding, heat welding, chemical bonding, and the like. As the number and size of the bonds increase, the elasticity of the foam-containing fluid handling layer 40 may decrease due to the increased rigidity of the bond areas. This stiffening effect may be reduced by using flexible adhesives to bond the fluid handling layer 40 to the garment. The shape and orientation of the bonds may also impact the overall stiffness of the fluid handling layer 40.

In the embodiments discussed thus far, the foam-containing fluid handling layer 40 is joined to the garment 10 in a stretched condition in both the front and rear regions 12, 14. Those skilled in the art will recognize, however, that the fluid handling layer 40 may be joined to the garment 10 in only the front region 12 or the rear region 14, or neither, and the remainder of the layer may be associated with the garment 10 in an unstretched condition (by, for example, directly joining the fluid handling layer 40 to the garment 10 or by capturing it in place) such that the foam-containing fluid handling layer 40 does not provide a lateral contracting force.

The present invention may be particularly suited for use with thin absorbent cores 34 (i.e., those that provide relatively high fluid absorbency as compared with their dry volume). Thin absorbent cores 34 typically comprise a relatively high volume of super absorbent material, when compared to the volume of fibrous filler or structure. Consequently, such absorbent cores are relatively thin and lightweight. Thin absorbent cores without the use of superabsorbent materials also can be used in the present invention. Such thin absorbent materials are disclosed, for example, in U.S. Pat. No. 5,803,920, the disclosure of which is incorporated by reference herein in its entirety.

The absorbent core 34 may be any absorbent means that is capable of absorbing or retaining liquids (e.g., menses and/or urine). The absorbent core 34 may be manufactured in a wide variety of sizes and shapes (e.g., rectangular, oval, hourglass, dog bone, asymmetric, etc.).

In one preferred embodiment, the absorbent core 34 is a laminate comprised of a layer of superabsorbent polymer material in the form of particles disposed between two air-laid tissues, first and second tissue layers (or "upper" and "lower" tissue layers). The first and second tissue layers contain the superabsorbent polymer material, improve lateral wicking of the absorbed exudates throughout the absorbent core 34 and provide a degree of absorbency. Other laminated absorbent core arrangements are disclosed in U.S. Pat. No. 6,068,620.

The absorbent core 34 may, however, be made from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; thermally bonded air-laid fibers; chemically stiffened, modified or crosslinked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these.

The configuration and construction of the absorbent core 34 also may be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core 34 should, however, be compatible with the design loading and the intended use of the absorbent article. Further, the size and absorbent capacity of the absorbent core 34 may be varied to accommodate different uses such as incontinence pads, pantiliners, regular sanitary napkins, overnight sanitary napkins, regular diapers, overnight diapers, adult diapers, pull-on pants, etc.

Exemplary absorbent structures for use as the absorbent core of the present invention are described in U.S. Pat. Nos. 4,950,264, 4,610,678, 4,834,735, 6,068,620, 6,099,950, 6,121,509, 6,171,291, 6,224,961, and European Patent Application No. 0 198 683, the disclosures of which are incorporated by reference herein in their entirety.

An additional benefit of the fluid handling layer 40 of the invention is that it may provide cushioning for the garment's user, especially when a foam material is included in the layer. Such cushioning may increase user comfort by making the garment 10 softer, and may help prevent injuries, especially in the case of users susceptible to bone injuries, such as some elderly persons. The thickness of the foam-containing fluid transfer layer 40 may, accordingly, be varied to provide cushioning for more sensitive areas of the user's body, such as the tailbone and the hips.

In addition to providing a thicker look and feel, in another embodiment of the invention, the fluid handling layer 40 may be selected to serve as a barrier between the absorbent core 34 and the topsheet 30. Super absorbent materials often are provided in a particulate form. The particles may have a variety of shapes and sizes, and some types of super absorbent materials may have particles with sharp edges or points that can pierce the topsheet 30, thereby causing discomfort. Preventing the SAP particles from piercing topsheet 30 will reduce the surface roughness and abrasive feel of the topsheet 30, which in turn should reduce the incidence of skin irritation.

The topsheet 30 is particularly susceptible to cuts or piercing during use when the wearer sits on the garment and during manufacture during which the article may be compressed at various points. The present invention preferably provides a physical barrier between the super absorbent particles in the absorbent core 34 and the topsheet 30, and may help to prevent sharp or pointed particles of super absorbent material from damaging the topsheet. This benefit may be even greater in garments having thin absorbent cores, in which case the decreased amount of padding in the form of fibrous structure and filler in the absorbent core 34, and the increased about of super absorbent particles, add to the likelihood of a puncture or cut.

In an embodiment employing the fluid handling layer 40 as a barrier to prevent cuts and punctures, the fluid handling layer 40 preferably comprises material having pore sizes, pore density, thickness, web strength and stiffness such that the super absorbent particles can not extend through the layer, even when it is compressed by the weight of the user. Using the guidelines provided herein, a person skilled in the art can design a suitable fluid handling layer 40, having the requisite pore sizes, pore density, thickness, web strength and stiffness to prevent super absorbent particles from extending there through.

The above benefits, and others, may be obtained by employing a properly selected elastic foam layer 40, and thin absorbent core 34. Other materials, such as thin pure pulp layers, airlaid bonded pulp layers, and bulky nonwoven layers, may be used to provide some of the above benefits, but may not provide all of the above benefits. In particular, none of these other materials can be readily used to provide elasticized front and rear regions 12, 14 for the garment 10.

Referring back to FIG. 1, the crotch region 16 may also include mechanical sealing devices to provide the garment 10 with a leak-proof fit around the wearer. In a preferred embodiment, the crotch edges 20 each have one or more elastic gathers 36 placed along them to help the crotch edges 20 contract about the contours of the wearer's body, thereby providing a leak-proof seal. Such gathers 36 are known in the art, and are disclosed, for example, in U.S. Pat. No. 5,830,203, issued to Suzuki et al., which is herein incorporated by reference in its entirety in a manner consistent with the present invention. The gathers 36 may extend into the rear waist band 14, and may extend as far as the front longitudinally distal edge 18.

In another preferred embodiment, standing leg gathers 38 are disposed on the topsheet 30. Standing leg gathers 38 are strips of material that rise vertically from the surface of the topsheet 30 to provide additional sealing to the garment 10. The standing leg gathers 38 may extend across all or part of the garment 10 along its longitudinal axis 100. Typically, one standing leg gather 38 is located on either side of the absorbent core 34. The standing leg gathers 38 may be made from folded portions of the topsheet 30 or backsheet 32, or may be made from additional strips of material. Each standing leg gather 38 may be equipped with one or more elastic elements to help seal the gather to the wearer's body. Standing leg gathers are known in the art, and disclosed in U.S. Pat. No. 5,292,316, issued to Suzuki, which is herein incorporated by reference in its entirety in a manner consistent with the present invention.

Any suitable elastic material may be used for the gathers 36 and the standing leg gathers 38. Preferably, the elastic material can be stretched to between more than 10% to 300% of its original length without losing its resilience. The elastic material used for the gathers 36 and standing leg gathers 38 may comprise an elastic film, a multidirectional elastic aggregate such as elastic webbing, netting, or scrim elastic, such as FLEXCEL™ Elastic Nonwoven Laminate, available from Kimberly-Clark Corporation, headquartered in Neenah, Wis., or strands or bands of suitable elastic materials, such as natural or synthetic rubber, urethane elastomers, spandex, LYCRA and elastic polymers. The elastics materials may be attached to the garment 10 in any of several ways known in the art. For example, the elastic materials may be ultrasonically bonded, heat/pressure sealed using a variety of bonding patterns, or glued to the diaper 10 using a variety of adhesives. Other performance enhancing devices, such as pockets, baffles, and openings in the topsheet also may be used with the present invention.

The absorbent article is optionally a diaper, incontinent brief, training pant, diaper holder, diaper liner, sanitary napkin, hygienic garment or combinations thereof. Diapers may include daytime diapers, nighttime diapers, long-term wear diapers, travel diapers, swimming diapers, daytime/nighttime diapers, male diapers, female diapers, unisex diapers, active diapers, seasonal diapers, cold weather diapers, warm weather diapers, medicated diapers, inactive diapers for newborns, specialty diapers for ill children having a higher incidence of runny BM, or combinations thereof.

The fluid handling layer 40 of the absorbent article embodiments of this invention can be comprised solely of one or more of the foam structures herein. For example, the fluid handling layer 40 may comprise a single unitary piece of foam shaped as desired or needed to best fit the type of absorbent article in which it is to be used. Alternatively, the fluid handling layer 40 may comprise a plurality of foam pieces or particles that may be adhesively bonded together or which may simply be constrained into an unbonded aggregate held together by an overwrapping of envelope tissue or by means of the topsheet and backing sheet of the absorbent article. In this regard, one of the foam materials may be an aliphatic polyurethane-derived foam material having the properties described herein, and additional foam materials may be any known foams, including the HIPE foams, and BASOTECT® foams.

In one embodiment involving a combination of the foam absorbent material herein and other absorbent materials, the absorbent articles herein may employ a multi-layer fluid handling layer 40 configuration wherein a core layer containing one or more foam structures of this invention may be used in combination with one or more additional separate core layers comprising conventional absorbent structures or materials. Such conventional absorbent structures or materials, for example, can include air-laid or wet-laid webs of wood pulp or other cellulosic fibers, carded thermal bonded fibers, non-woven sheets, and the like. Such conventional structures may also comprise conventional, e.g., large cell, absorbent foams or even sponges. Such conventional structures also may be used as the fluid handling layer 40, so long as the Strikethrough and Rewet characteristics of the invention are obtained.

As indicated hereinbefore, the fluid handling and mechanical characteristics of the specific foam materials described herein render such structures especially suitable for use in absorbent articles in the form of disposable diapers. Disposable diapers comprising the absorbent structures of the present invention may be made by using conventional diaper making techniques, but by replacing or supplementing the fluid handling layers typically used in conventional diapers with one or more structures of the present invention. It is preferred in this regard to employ a foam structure for the fluid handling layer, and such foam structures of this invention may be used in diapers in a single layer or, as noted hereinbefore, in various multiple layer core configurations.

Another preferred absorbent article that can utilize a foam absorbent structures of the present invention comprise form-fitting products such as training pants. Such form-fitting articles will generally include a nonwoven, flexible substrate fashioned into a chassis in the form of briefs or shorts. A fluid handling layer according to the present invention can then be affixed in the crotch area of such a chassis.

The invention now will be described in more detail with reference to the specifically preferred embodiments illustrated in the examples that follow.

EXAMPLES

Sample Preparation:

Absorbent articles were prepared for testing in accordance with the following procedure. Conventional absorbent articles were constructed using known apparatus and known materials, including a topsheet 30, backsheet 32, absorbent core 34 and fluid transfer layer 40. The conventional fluid transfer layer used herein for comparison purposes is a 40 g/m² carded thermal bond material adhered to the topsheet 30. The conventional diapers were Stage 4, Ultras, available from Paragon Trade Brands, Norcross, Ga. The diapers comprised a core that was about 110 mm wide, 380 mm long, had a basis weight of about 1,200 to about 1,440 g/m² (without the foam), a density of 1.14 g/cm³, and the concentration of SAP in fluff pulp was about 40% by weight.

Figure 8:
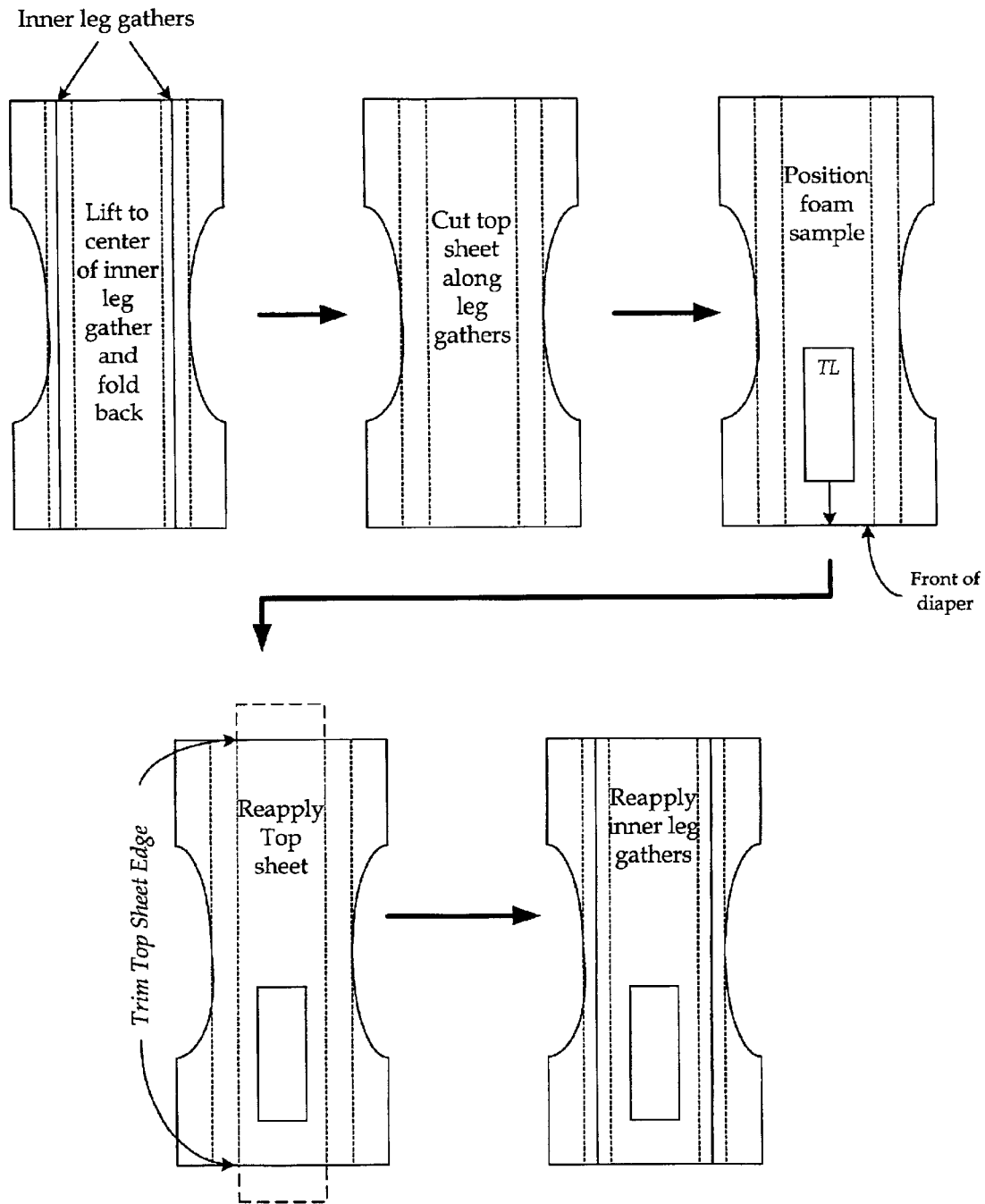
FIG. 8 is a schematic view of the method used to make by hand the absorbent garments used and tested in the examples.
Figure 9:
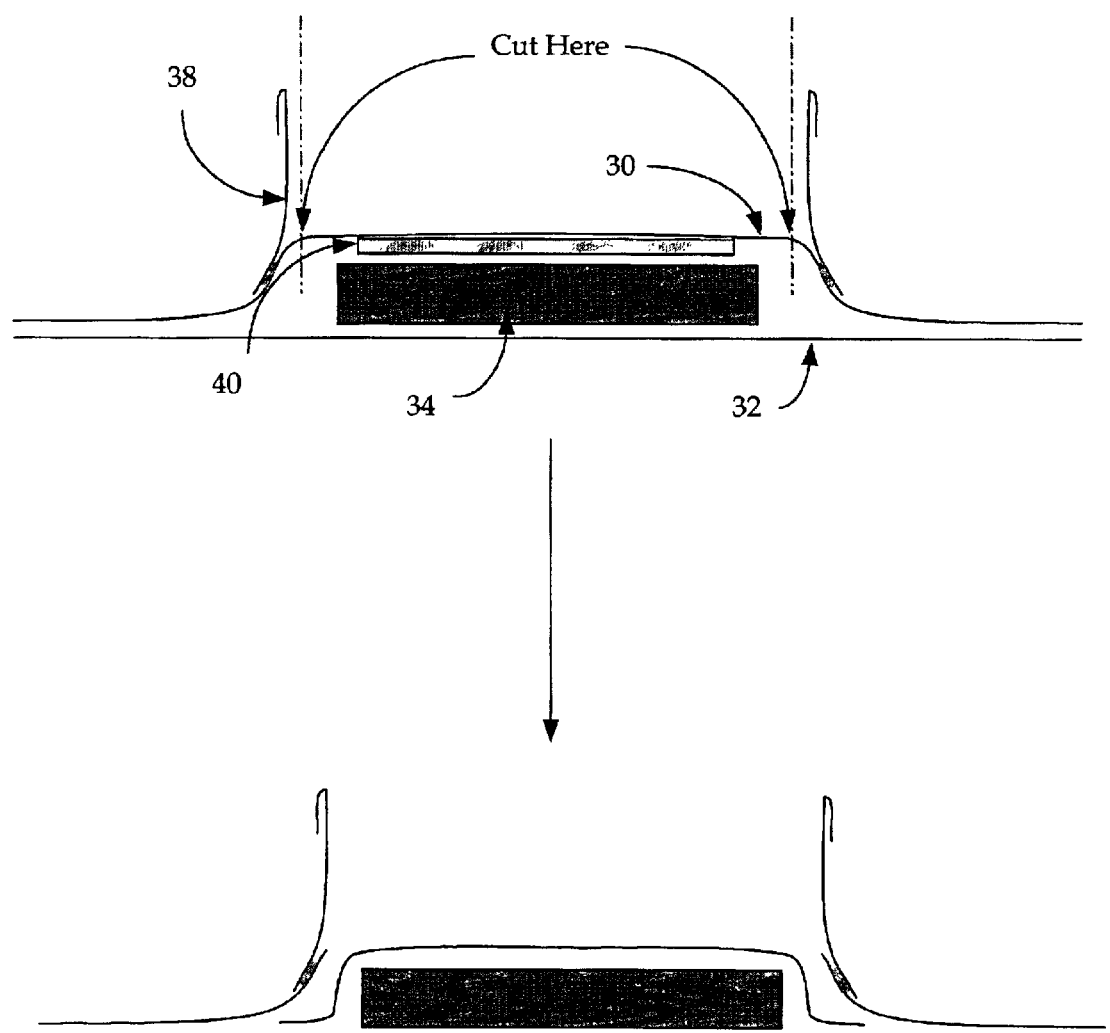
FIG. 9 is a side view of an absorbent article showing the cutting point made when making by hand the absorbent garments used and tested in the examples.

Referring now to FIGS. 8 and 9, the method of deconstructing the absorbent article, and then reconstructing it will be described. The conventional articles were de-constructed by removing the topsheet 30, and the fluid handling layer 40. The topsheet 30 was removed by first laying the garment flat, and clamping it to a stretch board. The inner leg gathers first are moved out of the way by folding them backwards, as shown in the upper left of FIG. 8. The folded portions of the inner leg gathers then can be clamped down, and the top sheet removed by cutting the top sheet along the leg gathers, as shown in the top center portion of FIG. 8. FIG. 9 provides a more detailed illustration of where the topsheet material is cut to enable its removal, along with the removal of the existing fluid transfer layer, if present.

A foam material that was cut into an approximate 90 mm×165 mm rectangle was positioned on the garment, as shown in the upper right portion of FIG. 8. It is most preferable that the foam sample be placed about 80 mm from the front of the diaper, as indicated by the down arrow in the upper right graphic of FIG. 8. Another topsheet material, made from the same non-woven material as the topsheet 30 in the conventional article, was prepared separately and cut to the dimensions of the conventional absorbent article. The topsheet, which preferably was prepared having a spiral glue adhesive in an amount of about 4 g/m², then was reapplied and adhered to the remainder of the conventional article to reconstruct the absorbent article, as shown in the bottom left portion of FIG. 8 The leg gathers then can be reapplied to the topsheet by tape adhesive or other joining mechanisms to reconstruct the garment, as shown in the bottom right of FIG. 8.

The reconstructed absorbent article then was folded and placed in a compression cell with a weight placed on top for greater than about 16 hours, preferably 24 hours, before testing. The weight is large enough to completely cover a folded diaper, and exerts a pressure of about 1080 Pa (0.16 psi).

Testing Procedures

Measuring Density

A foam sample first was prepared as follows. Foam samples of a predetermined size were cut from larger blocks of foam using a sharp reciprocating knife saw. Use of this or equivalent type of foam cutting device increased accuracy and specificity by serving to substantially eliminate edge flaws that may distort certain measurements made during the following test methods. Sample size specification also generally included a dimension for sample caliper or thickness. Caliper or thickness measurements for purposes of the present invention should be made when the foam sample is under a confining pressure of 350 Pa.

Density of the foam was determined using ASTM Method No. D3574-86. In particular, density measurements made according to the procedure were carried out on foam samples that had been preconditioned in a certain manner as specified in that test.

Density was determined by measuring both the dry mass of a given foam sample and its volume at 22±2° Celsius. Volume determination on larger foam samples were calculated from measurements of the sample dimensions made under no confining pressure. Dimensions of smaller foam samples may be measured using a dial-type gauge using a pressure on the dial foot of 350 Pa (0.05 psi). Density was calculated as mass per unit volume. For purposes of this invention, density is hereinafter expressed in terms of grams per cubic centimeter (g/cc).

Measuring the Change in Basis Weight

The change in Basis Weight simply is the difference between the basis weight of the foam sample prior to, and after washing. Thus, soluble materials present in the foam material will be "washed out" and a higher solubles content will generate a higher change in basis weight. A foam sample prepared by cutting the foam into about a 2 inch diameter circle was conditioned for 24 hours at TAPPI conditions (70° F., 50% relative humidity), and then weighed to determine its dry basis weight. A 100 mm by 50 mm beaker then was filled with a fresh saline Triton X test solution (fresh solution used each time) prepared as discussed below in the Strikethrough and Rewet test procedures. The sample then was held about 2 inches above the surface of the solution, parallel to the upper surface, and dropped into the beaker. The timer was started once the sample contacted the solution. The timer was stopped once the sample wetted out and the top surface of the sample was substantially wet with solution. The time was the drop time, which is related to the sink time, measured below. The samples then were retrieved from the solution, dried between paper towels, exposed to 32° C. heat for about 5 minutes in an oven, and then conditioned for 24 hours at TAPPI conditions (70° F., 50% relative humidity). The samples then were reweighed to calculate the final basis weight. The change in basis weight is the difference between the final basis weight and the initial dry basis weight. To the extent the foam materials contain soluble materials, the change in basis weight typically will be a negative number.

Measuring Sink Time and Weight Up-Take

Condition the foam material for about 24 hours at ambient temperature and relative humidity. Samples of the foam then were cut into 3×3×3 cm³ and laid on the surface of deionized water. The sample was weighed prior to dropping on the surface of deionized water. The time it took for the top surface of the sample cube to be substantially wet with water was the sink time. The wet foam samples then were weighed. The difference in weight was the weight up-take.

Measuring Cell Size and Hole Diameter

The foam cell size (diameter) was determined from the top of the foam sample (cell size A), and from the side of the sample (cell size B). The cell size, both cell size A and cell size B was measured by taking a statistical average on a foam sample of the diameter of as many cells possible (preferably up to about 30) using raster electron microscopy (REM), and visualizing the diameter by the eye. The cell size was represented in micrometers.

Hole diameter, which is related to cell size A and cell size B, was ascertained by measuring the hole diameter of as many cells as possible (again, up to about 30) using REM, and visual inspection, in both the A and B directions (e.g., on the top of the sample, and across the thickness of the sample). Like the cell size, the hole diameter is reported hereinafter in micrometers.

Measuring Tensile Strength

The tensile strength was measured in accordance with DIN EN ISO 1798, and was measured at two separate points on the foam sample, and then the value averaged. The value of tensile strength reported hereinafter is in kiloPascals.

Measuring Strikethrough and Rewet

Figure 3:
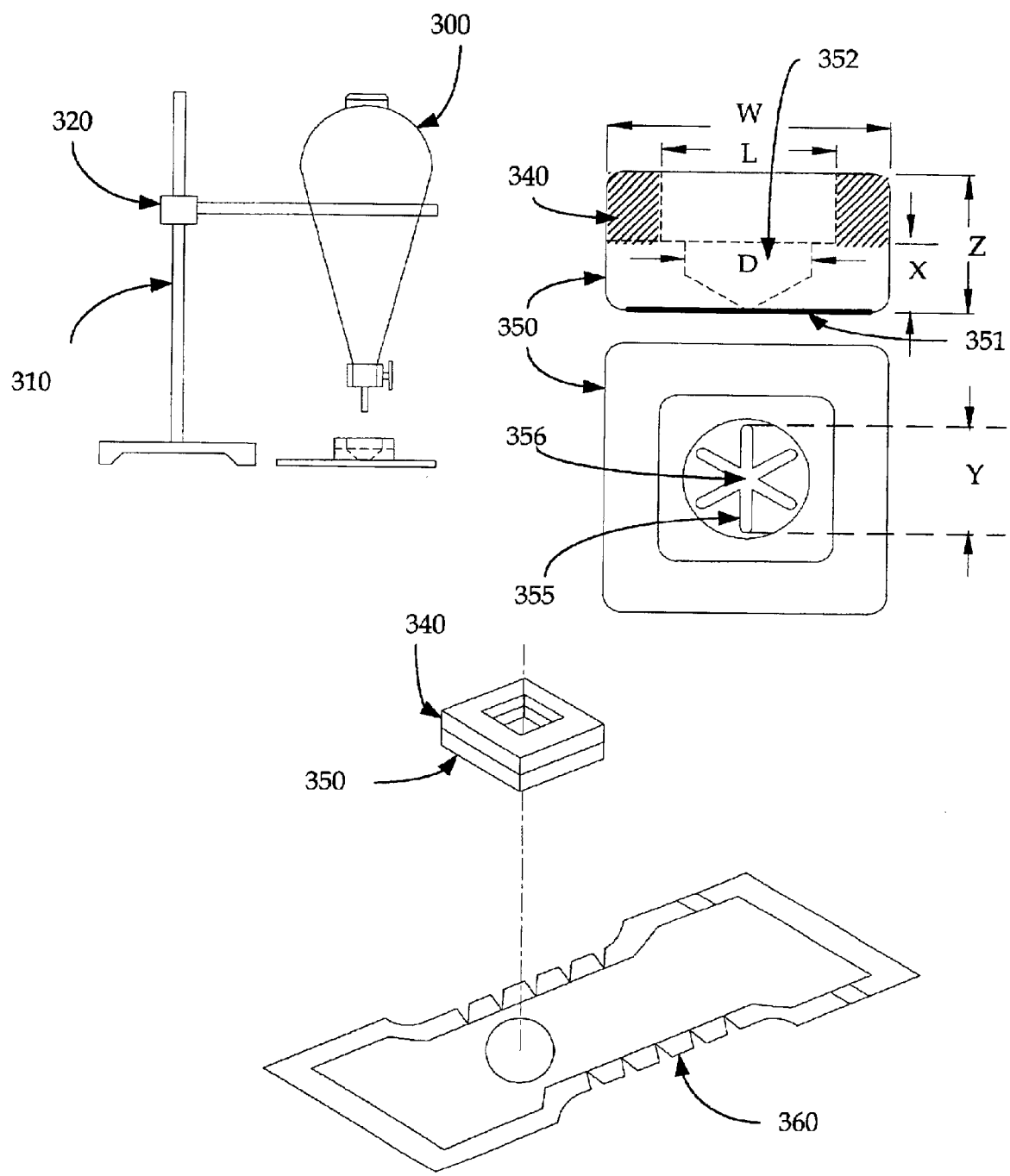
FIG. 3 is a schematic illustration of the apparatus used to measure the Strikethrough and Rewet characteristics of an absorbent article.

The apparatus used to measure strikethrough and rewet generally is shown in FIG. 3. The materials used include a burette (not shown) with discharge valve, preferably a 250 ml burette, and a separatory funnel 300, preferably a 150 ml separatory funnel having a 6–7 ml/second stopcock. The apparatus further included a stand 310 with a clamp 320, and a strikethrough plate 350, which included a plexiglas cover plate 340 (4"×4"). Other materials used in the strikethrough and rewet test included a 0.5 psi weight (2.5"×2.5"), Filter paper, Fisher Brand P8 filter paper cut to 4"×4", synthetic urine in the form of a 0.9% NaCl solution with 0.0025% Triton X-100 surfactant, a plexiglass coverplate 4"×4"×¼", a timer, a balance, and a stretch board with clamps 360.

As shown in FIG. 3, the strikethrough plate has specifically designed parameters. The strikethrough plate used to measure the Strikethrough and Rewet properties of the diapers meets the requirements set forth in edana Liquid Strike-Through Time Section 150.4-99, February 1999. Specifically, the strikethrough plate was constructed of a transparent acrylic sheet about 20 mm thick, which was placed on top of the strikethrough plate, having a thickness of about 17.8 mm. The strikethrough plate was fitted with corrosion-resistant electrodes 351 consisting of about 1.6 mm diameter platinum or stainless steel wire set in grooves of cross section of about 4.0 mm×7.0 mm cut into the base of the plate and fixed with quick-setting epoxy. The strikethrough plate 350 had an outlet opening at the top of the 17.8 mm deep bore 352, having a diameter D of a little more than about 25 mm. Thus, the values for X and D in FIG. 3 preferably are 17.8 mm, and 25 mm, respectively, although those skilled in the art will appreciate that the particular dimensions of D and X can vary. The bottom of the bore preferably had a center circular hub 356 with a diameter of about 1.9 mm with 6 symmetrically positioned spokes 355 extending about 11 mm from the hub. The value for Y in FIG. 3 therefore was about 22.225 mm, or about twice the length of each symmetrically positioned spoke 355. The slope of the bottom of bore 352 was about 25° from level.

The values for L, W, and Z in FIG. 3 also may vary, as will be appreciated by one of ordinary skill in the art. It was preferred that L be on the order of about 30 mm and W could be up to about 125 mm, but preferably was 70 mm. The overall thickness of the strikethrough plate, including strikethrough plate 350 and baseplate 340, designated by "Z" in FIG. 3, preferably was about 37.8 mm, whereby the baseplate 340 was about 20 mm thick.

Figure 7:
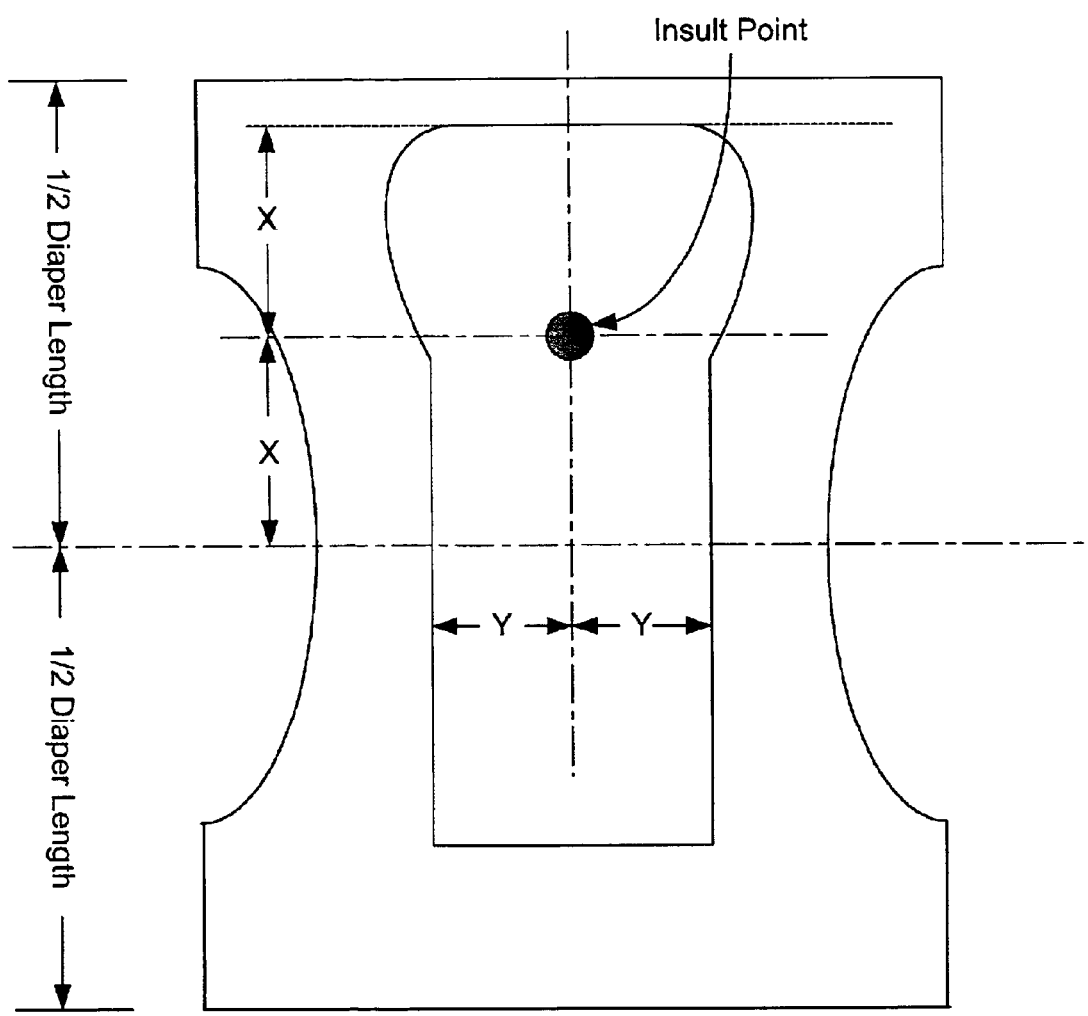
FIG. 7 is a schematic view of an absorbent article indicating where the insult point is for the Strikethrough and Rewet tests.

The samples preferably were prepared for the Strikethrough and Rewet test by selecting 6 mean weight diapers, prepared by the hand reconstruction sample preparation technique described above, that were free of lumps, creases, and wrinkles. The diapers were weighed to the nearest 0.1 g. The insult point then was marked as shown in FIG. 7, which typically is positioned ½ the distance from the midpoint of the diaper to the end point of the absorbent core, whereby half the distance is indicated by the letter "X" in FIG. 7. The insult point also was at the midpoint of the width of the absorbent core, whereby half the width of the absorbent core is indicated by the letter "Y" in FIG. 7.

The synthetic urine was prepared by weighing approximately 5 g of Triton X-100 into a clean, 200 ml flask. Then, about 18 g NaCl was weighed and transferred into the same 200 ml flask container with the Triton X-100, and diluted with de-ionized water to 200 ml liter. The solution then preferably was stirred. The test solutions were discarded if not used within seven days, or if the percent saline was not about 0.9% by weight, as measured using a refractometer.

Strikethrough and Rewet then were tested in accordance with the following procedure.

Stretch the diaper onto a stretch board with clamps 360, making sure there are no bumps or wrinkles in the diaper (see, FIG. 3). Then, mark the insult point on the diaper as shown in FIG. 7, and place the strikethrough plate 350 centered on the insult point. Referring again to FIG. 3, fill the separatory funnel 300 with 100 ml of test solution, and center the tip of the separatory funnel 300 a few mm above the strikethrough plate 350. Open the separatory funnel valve and start the timer at the exact same time, keeping the cavity of the strikethrough plate 352 completely full with solution to maintain constant pressure. When the complete 100 ml solution has been absorbed into the diaper, stop the timer, and record the Strikethrough value in seconds.

After recording the Strikethrough time, place the plexiglas coverplate 340 centered on the insult point, and place a 0.5 psi weight onto the cover plate. Leave the weight on the sample for 10 minutes. Then, weigh 18 g of filter paper, and record the weight to the nearest 0.1 gram. After about 10 minutes has elapsed, remove the 0.5 psi weight. Then, place the filter papers on the insult point, and replace the plexiglas coverplate 340 and the 0.5 psi weight on top of filter papers. Leave the cover plate and weight on for 10 minutes. After 10 minutes has elapsed, remove the cover plate 340, the weight, and the filter papers. Then, weigh the wet filter papers and record the value to the nearest 0.1 gram. This procedure from first striking the insult point with the 100 ml of solution, until the filter papers are weighed consists of an insult. Since this was the first time, it is denoted hereinafter as the first insult.

The procedure then is repeated on the same diaper sample for a second insult. For the second insult, however, about 50 grams of filter paper are used. The procedure then can be repeated on the same sample a third time for a third insult. For the third insult, however, about 72 grams of filter paper are used.

The Rewet is calculated by taking the difference in weight of the filter paper weighed before the plexiglas coverplate 340 and weight are placed thereon, and the filter paper weighed after ten minutes have elapsed with the plexiglas coverplate 340 and weight are placed thereon. The Rewet values are designated as the first insult Rewet, second insult Rewet, and third insult Rewet, respectively. The Strikethrough value is the amount of time, in seconds, taken for 100 ml of solution to completely absorb into the diaper.

EXAMPLES

A number of foam samples were obtained from BASF Aktiengesellschaft, Ludwigshafen, Germany. The samples were prepared in the same manner as the foam materials prepared in the examples of PCT WO01/55242, with the exception of samples A and B. In general, aliphatic isocyanates were reacted with polyetherols in the presence of a catalyst and complexed with an ethylenimine. Samples A and B were polyurethane foam materials made from aromatic diisocyanates. The foam materials had the physical properties listed in Table 1. A blank in Table 1 indicates that no value was obtained for that particular property.

Figure 4:
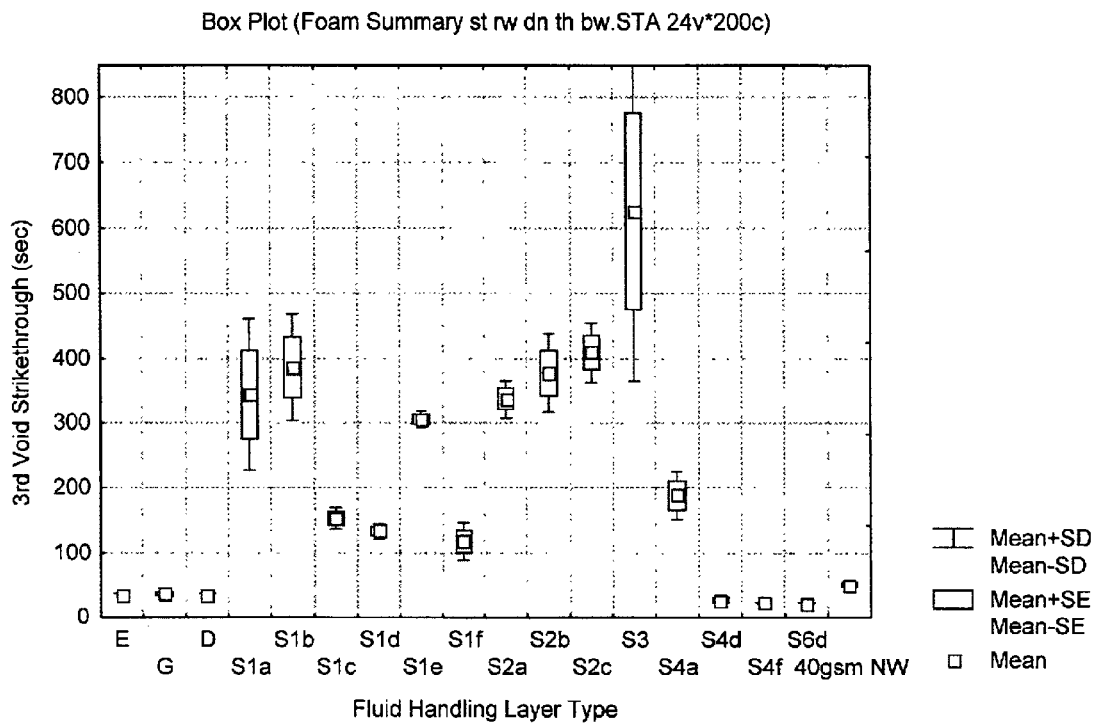
FIG. 4 is a graph illustrating the $3^{rd}$ insult Strikethrough results for a variety of materials used as fluid transport layers.
Figure 4:
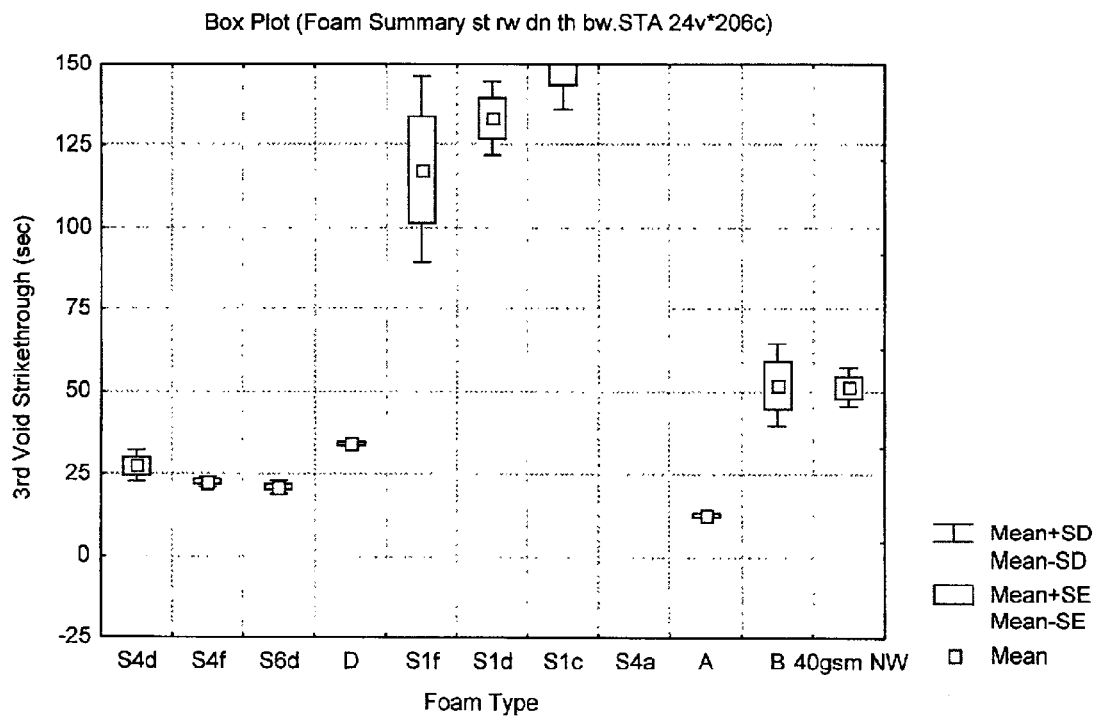
Figure 5:
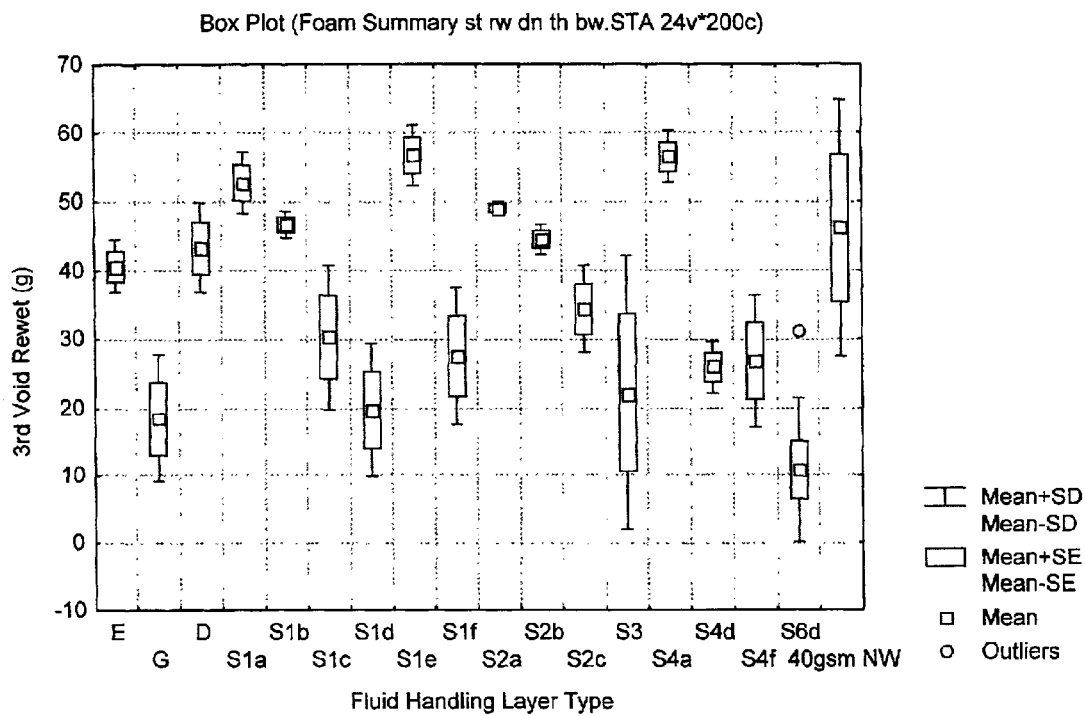
FIG. 5 is a graph illustrating the $3^{rd}$ insult Rewet results for a variety of materials used as fluid transport layers.
Figure 5:
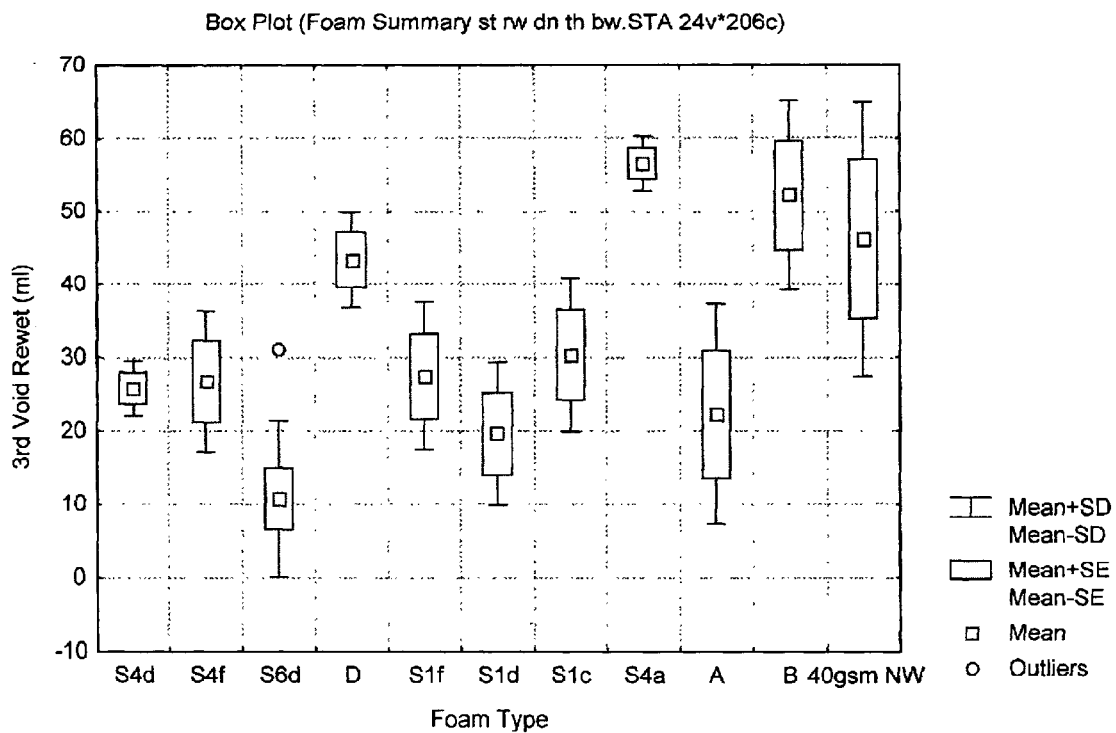

These foam materials were compared with a conventional 40 g/m$^2$ carded thermal bond material. Table 2 shows the Strikethrough and Rewet values for the first, second, and third insults, respectively. The results of Table 2 are shown graphically in FIGS. 4, 5, and 6.

TABLE 1

| Sample | Density (g/l) | Sink Time (sec) | Up-Take (g) | Tensile (kPa) | Cell A (µm) | Cell B (µm) | Hole Diameter (µm) | Delta Basis Weight (g/m$^2$) |
|---|---|---|---|---|---|---|---|---|
| A | 50 | 12 | 20 | 79 | — | — | — | |
| B | 20 | 6 | 42 | 58 | — | — | — | — |
| E | 67 | 37 | 20 | 66 | 472 | 296 | 112 | 1.5 |
| G | 81 | 75 | 17 | 71 | 407 | 349 | 131 | 0 |
| D | 72 | 47 | 19 | 69 | 398 | 354 | 126 | 9.0 |
| S1a | 81 | 38 | 12.5 | 46.1 | 257 | 240 | 113 | 36.9 |
| S1b | 78 | 25 | 13.2 | 42.1 | 265 | 194 | 69 | 44.28 |
| S1c | 81 | 36 | 15 | 148.5 | 312 | 233 | 69 | 3.69 |
| S1d | 79 | 36 | 15.6 | 83.7 | 259 | 216 | 96 | 1.23 |
| S1e | 81 | 53 | 14.9 | 105 | 274 | 243 | 46 | 39.36 |
| S1f | 79 | 130 | 12.8 | 212 | 330 | 241 | 79 | 17.22 |
| S2a | 73 | 36 | 13.9 | 67.5 | 309 | 280 | 85 | 31.98 |
| S2b | 70 | 30 | 15.2 | 72 | 303 | 189 | 79 | 33.21 |
| S2c | 71 | 32 | 16.6 | 54.2 | 440 | 217 | 88 | 23.37 |
| S3 | 76 | 50 | 14.5 | 49.4 | 307 | 275 | 73 | 38.13 |
| S4a | 67 | 50 | 19.4 | 14.2 | 400 | 330 | 158 | 87.33 |
| *S4d* | *61* | *28* | *22.4* | *39.9* | *580* | *320* | *220* | *14.76* |
| *S4f* | *62* | *44* | *22.9* | *47* | *640* | *310* | *245* | *3.69* |
| *S6d* | *57* | *280* | *23* | *72.4* | *750* | *522* | *370* | *1.23* |
| Control | | | | | | | | 4.92 |

The Strikethrough and Rewet values are taken for all six samples, and the reported values in the tables below (and in FIGS. 4, 5, and 6) represent the average for all six samples.

The aforementioned test procedures and sample preparations were carried out for a variety of different foam materials, as well as for a conventional fluid handling layer made of 40 gm/m$^2$ carded thermal bond material.

The units for the values in Table 1 are: density (g/l); sink time (seconds); up-take (grams); tensile strength kPa); cell A (µm); cell B (µm); hole diameter (µm); and delta basis weight was the absolute value in g/m$^2$. The materials used to prepare absorbent garments that had Strikethrough and Rewet values within the scope of the invention are highlighted in bold and italics in the Table above.

TABLE 2

| Sample | 1$^{st}$ Void Strikethrough (sec) | 2$^{nd}$ Void Strikethrough (sec) | 3$^{rd}$ Void Strikethrough (sec) | 1$^{st}$ Void Rewet (g) | 2$^{nd}$ Void Rewet (g) | 3$^{rd}$ Void Rewet (g) |
|---|---|---|---|---|---|---|
| A | *13* | *13* | *13* | *0.52* | *4.16* | *22.29* |
| B | 17 | 43 | 52 | 0.46 | 19.10 | 52.21 |
| E | 21 | 30 | 34 | 0.50 | 14.0 | 40.61 |
| G | 28 | *36* | 37 | *0.98* | *2.42* | *18.40* |
| D | 22 | 30 | 34 | 0.52 | 13.73 | 43.31 |
| S1a | 46 | 287 | 345 | 1.93 | 30.00 | 52.76 |
| S1b | 52 | 325 | 387 | 2.56 | 29.45 | 46.67 |
| S1c | 56 | 134 | 153 | 0.48 | 6.38 | 30.33 |
| S1d | 79 | 119 | 133 | 0.36 | 0.62 | 19.64 |
| S1e | 41 | 208 | 306 | 1.97 | 32.00 | 56.78 |

TABLE 2-continued

| Sample | 1st Void Strikethrough (sec) | 2nd Void Strikethrough (sec) | 3rd Void Strikethrough (sec) | 1st Void Rewet (g) | 2nd Void Rewet (g) | 3rd Void Rewet (g) |
|---|---|---|---|---|---|---|
| S1f | 51 | 99 | 118 | 0.37 | 4.38 | 27.51 |
| S2a | 97 | 308 | 338 | 7.08 | 30.98 | 48.99 |
| S2b | 81 | 302 | 378 | 2.23 | 23.96 | 44.50 |
| S2c | 68 | 428 | 410 | 0.67 | 18.58 | 34.38 |
| s3 | 95 | 510 | 626 | 3.06 | 21.45 | 33.10 |
| s4a | 45 | 174 | 188 | 3.53 | 35.27 | 56.56 |
| *S4d* | *19* | *22* | *28* | *0.29* | *8.41* | *25.84* |
| *S4f* | *19* | *21* | *23* | *0.38* | *6.39* | *26.71* |
| *S6d* | *27* | *24* | *21* | *0.31* | *1.11* | *10.77* |
| control | 27 | 38 | 51 | 0.09 | 6.57 | 46.14 |

Figure 6:
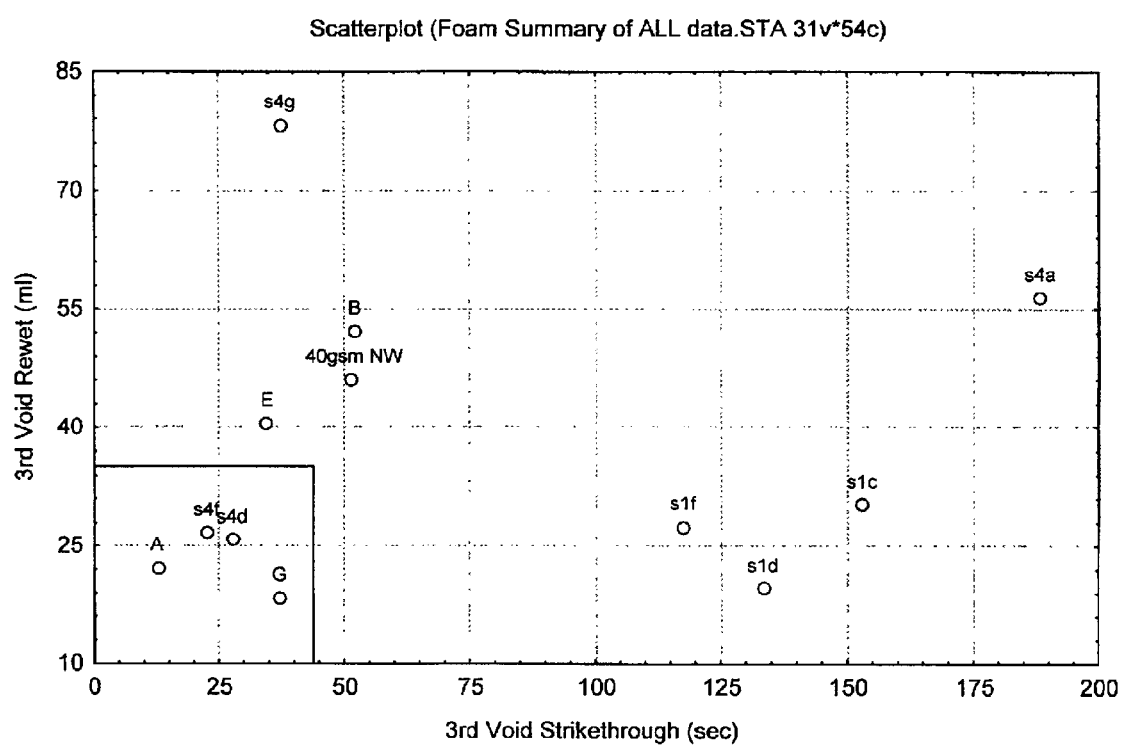
FIG. 6 is a graph illustrating the $3^{rd}$ insult Strikethrough and $3^{rd}$ insult Rewet results for a variety of materials used as fluid transport layers.

Inventive foam materials are bold and italicized in Table 2. As shown in Table 2, and as can be seen in FIG. 6, foams in accordance with the present invention, when used as at least part of a fluid transfer layer 40 in an absorbent article 10, provide a third insult Strikethrough of less than about 45 seconds, and a third insult Rewet of less than about 35 grams. Such materials thereby enable the absorbent article to more rapidly absorb the fluid, and then retain the fluid under load to prevent rewet, prevent leakage, and help maintain the skin dry and healthy.

The present invention has been described in connection with the preferred embodiments. These embodiments, however, are merely for example and the invention is not restricted thereto. Any examples described herein are illustrative of preferred embodiments of the inventive subject matter and are not to be construed as limiting the inventive subject matter thereto. It will be understood by those skilled in the art that other variations and modifications can easily be made within the scope of the invention as defined by the appended claims. All documents referred to in the above description are incorporated by reference herein in their entirety.

What is claimed is:

1. An absorbent article comprising:
   a substantially impermeable backsheet;
   a permeable topsheet;
   an absorbent core disposed between the substantially impermeable backsheet and permeable topsheet; and
   a foam fluid handling layer,
   whereby the foam fluid handling layer is disposed between the permeable topsheet and the absorbent core, and
   wherein the absorbent article has a third insult Strikethrough of less than about 45 seconds, and a third insult Rewet of less than about 35 grams; and
   wherein the fluid handling layer is comprised of a polyurethane foam made from at least an aliphatic isocyanate.

2. The absorbent article of claim 1, wherein the absorbent article is selected from the group consisting of a diaper, an incontinent brief, a training pant, a diaper holder, a diaper liner, a sanitary napkin, a hygienic garment, a swimming diaper, or combinations thereof.

3. The absorbent article of claim 1, wherein the third insult Strikethrough is less than about 40 seconds.

4. The absorbent article of claim 3, wherein the third insult Strikethrough is less than about 35 seconds.

5. The absorbent article of claim 1, wherein the third insult Rewet is less than about 30 grams.

6. The absorbent article of claim 5, wherein the third insult Rewet is less than about 25 grams.

7. The absorbent article of claim 1, wherein the aliphatic isocyanate is at least one isocyanate selected from the group consisting of hexamethylene diisocyanate, hexamethylene triisocyanate, bicycloheptane triisocyanate, undecanetriisocyanate, lysine ester triisocyanate, isophorone diisocyanate, dicyclohexylmethane diisocyanate, methylcyclohexane diisocyanate, dimethylcyclohexane diisocyanate, xylylene diisocyanate, tetramethylxylylene diisocyanate, their dimers, their trimers, and mixtures thereof.

8. The absorbent article of claim 7, wherein the aliphatic isocyanate is hexamethylene diisocyanate.

9. The absorbent article of claim 1, wherein the aliphatic isocyanate is reacted with a polyester alcohol.

10. The absorbent article of claim 9, wherein the polyester alcohol is a polyetherol having a molecular weight within the range of from about 1,000 to about 6,000 g/mol, and a functionality of from about 2 to about 8.

11. The absorbent article of claim 9, wherein the polyurethane is complexed with a complexing agent selected from the group consisting of ethylenimine, polyethylenimine, polyvinylamine, carboxy-methylated polyethylenimines, phosphono-methylated polyethylenimines, quaternized polyethylenimines and/or dithiocarbamitized polyethylenimines.

12. The absorbent article of claim 11, wherein the complexing agent is a polyethylenimine having a molecular weight within the range of from about 500 to about 30,000 g/mol.

13. The absorbent article of claim 9, wherein the polyester alcohol is selected from the group consisting of polyether polyols, ethylene glycol, propylene glycol, glycerol, hexanetriol, triethanolamine, ethylene oxide, propylene oxide, butylene oxide, polytetramethylene ether glycol, lactone-type polyester polyols, polyol compounds obtained by condensing a dihydric or trihydric alcohol with s hydroxycarboxylic acid, polyol compounds obtained by condensing dicarboxylic acids with diols, condensed polyester polyols obtained by adding acid anhydrides with diols, and mixtures thereof.

14. The absorbent article of claim 9, wherein the aliphatic isocyanate and polyester alcohol are reacted in the presence of a catalyst selected from the group consisting of tin diacetate, tin dioctoate, dialkyltin dilaurate, triethylamine, pentamethyldiethylenetriamine, bis(dimethylaminoethyl) ether, 1,2-dimethylimidazole, dimethylcyclohexylamine, dimethylbenzylamine, triethylenediamine, and mixtures thereof.

15. The absorbent article as claimed in claim 1, wherein the foam has a sink time of more than 20 seconds.

16. The absorbent article as claimed in claim 1, wherein the foam has a liquid up-take of from about 10 to about 30 grams.

17. The absorbent article as claimed in claim 1, wherein the foam has a tensile strength of from about 25 to about 100 kPa.

18. The absorbent article as claimed in claim 1, wherein the foam has a cell size from the top surface of the foam (cell size A) of from about 400 to about 1,000 μm.

19. The absorbent article as claimed in claim 1, wherein the foam has a cell size from the side surface of the foam (cell size B) of from about 300 to about 550 μm.

20. The absorbent article as claimed in claim 1, wherein the foam has a hole diameter within the range of from about 125 to about 400 μm.

21. The absorbent article as claimed in claim 1, wherein the foam as an absolute value change in basis weight from dry basis weight to wet basis weight of less than about 20 g/m².

22. An absorbent garment comprising:
a substantially impermeable backsheet and a permeable topsheet defining a front waist portion and a rear waist portion, said front waist portion and said rear waist portion cooperating to form a waist opening;
a crotch region formed between the front waist portion and the rear waist portion;
a pair of leg openings on opposed sides of the crotch region;
an absorbent core; disposed between the substantially impermeable backsheet and the permeable topsheet at the crotch region; and
a foam fluid handling layer comprising a foam made from at least an aliphatic isocyanate,
whereby the foam fluid handling layer is disposed between the permeable topsheet and the absorbent core, and
wherein the absorbent article has a third insult Strikethrough of less than about 45 seconds, and a third insult Rewet of less than about 35 grams.

23. The absorbent article of claim 22, wherein the foam fluid handling layer is a polyurethane foam fluid handling layer made from at least an aliphatic isocyanate.

24. The absorbent article of claim 22, wherein the foam fluid handling layer is made from at least one polymer selected from the group consisting of a polyurethane, a polyethylene, a polypropylene, a polyacrylic, a polyamide, a polyvinyl chloride, an epoxy, a polystyrene, a melamine-formaldehyde polymer, and combinations thereof.

25. The absorbent article of claim 22, wherein the foam fluid handling layer is comprised of at least a polyurethane polymer or a melamine-formaldehyde polymer.

26. The absorbent article of claim 24, wherein the polymer is a melamine-formaldehyde polymer.

27. The absorbent article of claim 22, wherein the foam has a density within the range of from about 20 to about 700 grams/liter.

28. The absorbent article of claim 22, wherein the foam additionally comprises a stabilizing agent.

29. The absorbent article of claim 22, wherein the foam additionally comprises at least one additive selected from the group consisting of surfactants, fillers, additives, or combinations thereof.

30. The absorbent article of claim 29, wherein the additive is selected from the group consisting of a flame retardant, a reinforcing agent, an auxiliary blowing agent, a medicament, a fragrance, a colorant, a cleaner, an abrasive, and combinations thereof.

31. The absorbent article of claim 22, wherein the absorbent article is selected from the group consisting of a diaper, an incontinent brief, a training pant, a diaper holder, a diaper liner, a sanitary napkin, a hygienic garment, a swimming diaper, or combinations thereof.

32. The absorbent article of claim 22, wherein the third insult Strikethrough is less than about 40 seconds.

33. The absorbent article of claim 32, wherein the third insult Strikethrough is less than about 35 seconds.

34. The absorbent article of claim 22, wherein the third insult Rewet is less than about 30 grams.

35. The absorbent article of claim 34, wherein the third insult Rewet is less than about 25 grams.

36. The absorbent article of claim 23, wherein the aliphatic isocyanate is at least one isocyanate selected from the group consisting of hexamethylene diisocyanate, hexamethylene triisocyanate, bicycloheptane triisocyanate, undecanetriisocyanate, lysine ester triisocyanate, isophorone diisocyanate, dicyclohexylmethane diisocyanate, methylcyclohexane diisocyanate, dimethylcyclohexane diisocyanate, xylylene diisocyanate, tetramethylxylylene diisocyanate, their dimers, their trimers, and mixtures thereof.

37. The absorbent article of claim 36, wherein the aliphatic isocyanate is hexamethylene diisocyanate.

38. The absorbent article of claim 23, wherein the aliphatic isocyanate is reacted with a polyester alcohol.

39. The absorbent article of claim 38, wherein the polyester alcohol is a polyetherol having a molecular weight within the range of from about 1,000 to about 6,000 g/mol, and a functionality of from about 2 to about 8.

40. The absorbent article of claim 38, wherein the polyurethane is complexed with a complexing agent selected from the group consisting of ethylenimine, polyethylenimine, polyvinylamine, carboxy-methylated polyethylenimines, phosphono-methylated polyethylenimines, quaternized polyethylenimines and/or dithiocarbamitized polyethylenimines.

41. The absorbent article of claim 40, wherein the complexing agent is a polyethylenimine having a molecular weight within the range of from about 500 to about 30,000 g/mol.

42. The absorbent article of claim 38, wherein the polyester alcohol is selected from the group consisting of polyether polyols, ethylene glycol, propylene glycol, glycerol, hexanetriol, triethanolamine, ethylene oxide, propylene oxide, butylene oxide, polytetramethylene ether glycol, lactone-type polyester polyols, polyol compounds obtained by condensing a dihydric or trihydric alcohol with s hydroxycarboxylic acid, polyol compounds obtained by condensing dicarboxylic acids with diols, condensed polyester polyols obtained by adding acid anhydrides with diols, and mixtures thereof.

43. The absorbent article of claim 38, wherein the aliphatic isocyanate and polyester alcohol are reacted in the presence of a catalyst selected from the group consisting of tin diacetate, tin dioctoate, dialkyltin dilaurate, triethylamine, pentamethyldiethylenetriamine, bis (dimethylaminoethyl) ether, 1,2-dimethylimidazole, dimethylcyclohexylamine, dimethylbenzylamine, triethylenediamine, and mixtures thereof.

44. The absorbent article as claimed in claim 23, wherein the foam has a sink time of more than 20 seconds.

45. The absorbent article as claimed in claim 23, wherein the foam has a liquid up-take of from about 10 to about 30 grams.

46. The absorbent article as claimed in claim 23, wherein the foam has a tensile strength of from about 25 to about 100 kPa.

47. The absorbent article as claimed in claim 23, wherein the foam has a cell size from the top surface of the foam (cell size A) of from about 400 to about 1,000 µm.

48. The absorbent article as claimed in claim 23, wherein the foam has a cell size from the side surface of the foam (cell size B) of from about 300 to about 550 µm.

49. The absorbent article as claimed in claim 23, wherein the foam has a hole diameter within the range of from about 125 to about 400 µm.

50. The absorbent article as claimed in claim 23, wherein the foam as an absolute value change in basis weight from dry basis weight to wet basis weight of less than about 20 g/m².

51. A method of preparing an absorbent article comprising:
providing a topsheet material and a backsheet material;
disposing between the topsheet and backsheet materials an absorbent core;
disposing between the topsheet and the absorbent core a foam fluid transport layer,
whereby the absorbent article has a third insult Strikethrough of less than about 45 seconds, and a third insult Rewet of less than about 35 grams; and
wherein the fluid handling layer is a polyurethane foam fluid handling layer made from at least an aliphatic isocyanate.

52. The method of claim 51, wherein the absorbent article is selected from the group consisting of a diaper, an incontinent brief, a training pant, a diaper holder, a diaper liner, a sanitary napkin, a hygienic garment, a swimming diaper, or combinations thereof.

53. The method of claim 51, wherein the third insult Strikethrough is less than about 40 seconds.

54. The method of claim 53, wherein the third insult Strikethrough is less than about 35 seconds.

55. The method of claim 51, wherein the third insult Rewet is less than about 30 grams.

56. The method of claim 55, wherein the third insult Rewet is less than about 25 grams.

57. The method of claim 51, wherein the aliphatic isocyanate is at least one isocyanate selected from the group consisting of hexamethylene diisocyanate, hexamethylene triisocyanate, bicycloheptane triisocyanate, undecanetriisocyanate, lysine ester triisocyanate, isophorone diisocyanate, dicyclohexylmethane diisocyanate, methylcyclohexane diisocyanate, dimethylcyclohexane diisocyanate, xylylene diisocyanate, tetramethylxylylene diisocyanate, their dimers, their trimers, and mixtures thereof.

58. The method of claim 57, wherein the aliphatic isocyanate is hexamethylene diisocyanate.

59. The method of claim 51, wherein the aliphatic isocyanate is reacted with a polyester alcohol.

60. The method of claim 59, wherein the polyester alcohol is a polyetherol having a molecular weight within the range of from about 1,000 to about 6,000 g/mol, and a functionality of from about 2 to about 8.

61. The method of claim 59, wherein the polyurethane is complexed with a complexing agent selected from the group consisting of ethylenimine, polyethylenimine, polyvinylamine, carboxy-methylated polyethylenimines, phosphono-methylated polyethylenimines, quaternized polyethylenimines and/or dithiocarbamitized polyethylenimines.

62. The method of claim 61, wherein the complexing agent is a polyethylenimine having a molecular weight within the range of from about 500 to about 30,000 g/mol.

63. The absorbent article of claim 59, wherein the polyester alcohol is selected from the group consisting of polyether polyols, ethylene glycol, propylene glycol, glycerol, hexanetriol, triethanolamine, ethylene oxide, propylene oxide, butylene oxide, polytetramethylene ether glycol, lactone-type polyester polyols, polyol compounds obtained by condensing a dihydric or trihydric alcohol with s hydroxycarboxylic acid, polyol compounds obtained by condensing dicarboxylic acids with diols, condensed polyester polyols obtained by adding acid anhydrides with diols, and mixtures thereof.

64. The method of claim 59, wherein the aliphatic isocyanate and polyester alcohol are reacted in the presence of a catalyst selected from the group consisting of tin diacetate, tin dioctoate, dialkyltin dilaurate, triethylamine, pentamethyldiethylenetriamine, bis(dimethylaminoethyl) ether, 1,2-dimethylimidazole, dimethylcyclohexylamine, dimethylbenzylamine, triethylenediamine, and mixtures thereof.

65. The method as claimed in claim 51, wherein the foam has a sink time of more than 20 seconds.

66. The method as claimed in claim 51, wherein the foam has a liquid up-take of from about 10 to about 30 grams.

67. The method as claimed in claim 51, wherein the foam has a tensile strength of from about 25 to about 100 kPa.

68. The method as claimed in claim 51, wherein the foam has a cell size from the top surface of the foam (cell size A) of from about 400 to about 1,000 µm.

69. The method as claimed in claim 51, wherein the foam has a cell size from the side surface of the foam (cell size B) of from about 300 to about 550 µm.

70. The method as claimed in claim 51, wherein the foam has a hole diameter within the range of from about 125 to about 400 µm.

71. The method as claimed in claim 51, wherein the foam as an absolute value change in basis weight from dry basis weight to wet basis weight of less than about 20 g/m².

* * * * *